P

US008754051B2

(12) United States Patent
Johnson et al.

(10) Patent No.: US 8,754,051 B2
(45) Date of Patent: Jun. 17, 2014

(54) PEPTIDE MODULATORS OF THE δPKC INTERACTION WITH THE D SUBUNIT OF F₁FO ATP SYNTHASE/ATPASE AND USES THEREOF

(75) Inventors: John A. Johnson, Harlem, GA (US); Tiffany Tuyen M. Nguyen, Rockville, MD (US); Mourad Ogbi, Martinez, GA (US)

(73) Assignee: Georgia Regents Research Institute, Inc., Augusta, GA (US)

( * ) Notice: Subject to any disclaimer, the term of this patent is extended or adjusted under 35 U.S.C. 154(b) by 0 days.

(21) Appl. No.: 13/401,035

(22) Filed: Feb. 21, 2012

(65) Prior Publication Data
US 2012/0283182 A1 Nov. 8, 2012

Related U.S. Application Data

(63) Continuation of application No. PCT/US2010/002268, filed on Aug. 18, 2010.

(60) Provisional application No. 61/396,375, filed on May 26, 2010, provisional application No. 61/274,431, filed on Aug. 18, 2009.

(51) Int. Cl.
*A61K 38/16* (2006.01)
*C07K 14/00* (2006.01)

(52) U.S. Cl.
CPC .................. *A61K 38/16* (2013.01); *C07K 14/00* (2013.01); *C07K 2319/00* (2013.01)
USPC ......................................... 514/21.3; 530/324

(58) Field of Classification Search
CPC ....... A61K 38/16; A61K 38/00; C07K 14/00; C07K 2319/00; C12N 9/14
See application file for complete search history.

(56) References Cited

U.S. PATENT DOCUMENTS 5,962,646 A * 10/1999 Hillman et al. ............... 530/350

OTHER PUBLICATIONS

Higuti et al, The Complete Amino Acid Sequence of Subunit d of Rat Liver Mitochondrial H+-ATP Synthase, J. Biochem., 1993, 114, pp. 714-717.*
Sidhu et al, Interaction of thrombin with mammalian platele, Am. J. Physiol., 1979, 237, pp. H353-H358.*
Fischer, Cellular Uptake Mechanisms and Potential Therapeutic Utility of Peptidic Cell Delivery Vectors: Progress 2001-2006, Medicinal Research Reviews, 2007, 27, pp. 755-795.*
Goto et al, Nucleotide sequence of cDNA for rat brain and liver cytochrome c oxidase subunit IV, Nucleic Acids Research, 1989, 17, p. 2851.*
Lithgow, Targeting of proteins to mitochondria, FEBS Letters, 2000, 476, pp. 22-26.*

Hopp et al, A short polypeptide marker sequence useful for recombinant protein identification and purification, Biotechnology, 1988, 6, pp. 1204-1210.*
An, et al., "Role of changes in cardiac metabolism in development of diabetic cardiomyopathy" . Am. J. Physiol. Heart Circ. Physiol. 291:H1489-H1506 (2006).
Arikawa, et al., "Effects of insulin replacements, inhibitors of angiotensin, and PKCbeta's actions to normalize cardiac gene expression and fuel metabolism in diabetic rats", Diabetes. 56:1410-20 (2007).
Awaji, et al., "Isoenzyme profiles of creatine kinase, lactate dehydrogenase, and aspartate aminotransferase in the diabetic heart: comparison with hereditary and catecholamine cardiomyopathies", Cardiovasc. Res., 24:547-54 (1990).
Boudina, et al., "Reduced mitochondrial oxidative capacity and increased mitochondrial uncoupling impair myocardial energetics in obesity", Circulation ,112:2686-95 (2005).
Boudina, at al.,"Diabetic cardiomyopathy revisited", Circulation, 115:3213-23 (2007).
Boudina and Abel, "Mitochondrial uncoupling: a key contributor to reduced cardiac efficiency in diabetes" , Physiology (Bethesda), 21:250-8 (2006).
Brix, et al., "Distribution of binding sequences for the mitochondrial import receptors Tom20, Tom22, and Tom70 in a presequence-carrying preprotein and a non-cleavable preprotein", J. Biol. Chem 274:16522-30 (1991).
Budas, et al., "Cardioprotective mechanisms of PKC isozyme-selective activators and inhibitors in the treatment of ischemia-reperfusion injury", Pharmacol. Res., 55(6):523-36 (2007).
Chen, et al., "Opposing cardioprotective actions and parallel hypertrophic effects of delta PKC and epsilon PKC", PNAS, 98:11114-9 (2001).
Collinson and Gaze, "Biomarkers of cardiovascular damage and dysfunction—an overview", Heart Lung Circ., 16 Suppl 3:S71-S82 (2007).
Conricode, et al., "Activation of phospholipase D by protein kinase C. Evidence for a phosphorylation-independent mechanism", J. Biol. Chem., 267:7199-202 (1992).

(Continued)

*Primary Examiner* — Julie Ha
*Assistant Examiner* — Li Ni Komatsu
(74) *Attorney, Agent, or Firm* — Pabst Patent Group LLP

(57) ABSTRACT

The present invention provides isolated or synthetic peptides derived from the d subunit of mammalian F₁Fo ATP synthase (dF₁Fo) protein for the purposes of tissue protection and improved energy production following acute injury from ischemia/reperfusion or other toxic insults, or in chronic diseases such as diabetes and cancer. The major focus of the patent protection will be 2 peptides comprising an amino acid sequence having at least 75% sequence identity to SEQ ID NO: 1 or SEQ ID NO: 2 and pharmaceutical compositions thereof. However, additional peptide sequences within the dF₁Fo protein may also have efficacies in these disease states and therefore all peptides shown in the Figures of this application (combined with the human immunodeficiency virus (HIV)-Tat protein transduction, cytochrome oxidase subunit IV (COIV) mitochondrial targeting and Flag domains) are included for their efficacies in these conditions.

4 Claims, 16 Drawing Sheets

(56) References Cited

OTHER PUBLICATIONS

Gray, et al., "A selective epsilon-protein kinase C antagonist inhibits protection of cardiac myocytes from hypoxia-induced cell death", J.Biol. Chem., 272:30945-951 (1997).

Guo, et al., "Protein kinase C-epsilon coimmunoprecipitates with cytochrome oxidase subunit IV and is associated with improved cytochrome-c oxidase activity and cardioprotection", Am. J. Physiol. Heart Circ, Physiol. 293:H2219-H2230 (2007).

Hutteman, et al. "Regulation of oxidative phosphorylation, the mitochondrial membrane potential, and their role in human disease",, J. Bioenerg. Biomembr., 40:445-56 (2008).

Kolar, et al., "Role of oxidative stress in PKC-delta upregulation and cardioprotection induced by chronic intermittent hypoxia", Am J Physiol Heart Circ Physiol., 292(1):H224-30 (2006).

Kuo, et al., "Defective oxidative metabolism of heart mitochondria from genetically diabetic mice", Diabetes, 32:781-7 (1983).

Malhotra, et al., "PKC-{epsilon}-dependent survival signals in diabetic hearts", Am. J. Physiol. Heart Circ. Physiol., 289:H1343-H1350 (2005).

Neely, et al., "Myocardial utilization of carbohydrate and lipids", Prog. Cardiovasc. Dis., 15:289-329 (1972).

Nguyen, et al., "Delta protein kinase C interacts with the d subunit of the F1F0 ATPase in neonatal cardiac myocytes exposed to hypoxia or phorbol ester. Implications for F1F0 ATPase regulation", J. Biol. Chem., 283:29831-40 (2008).

Nguyen, et al., "Modulation of the protein kinase Cdelta interaction with the "d" subunit of F1F0-ATP synthase in neonatal cardiac myocytes: development of cell-permeable, mitochondrially targeted inhibitor and facilitator peptides", J Biol Chem, 285(29):22164-73 (2010a).

Nguyen, et al., "Attenuation of the hypoxia-Induced protein kinase Cdelta interaction with the 'd' subunit of F1Fo-ATP synthase in neonatal cardiac myocytes: implications for energy preservation and survival", Biochem J., 429(2):335-45 (2010b).

Nishikawa, et al., "Association of protein kinase Cmu with type II phosphatidylinositol 4-kinase and type I phosphatidylinositol-4-phosphate 5-kinase", J.Biol. Chem., 273:23126-33 (1998).

Ogbi, et al., "Cytochrome c oxidase subunit IV as a marker of protein kinase Cepsilon function in neonatal cardiac myocytes: implications for cytochrome c oxidase activity" Biochem. J., 382:923-32 (2004).

Ogbi and Johnson, "Protein kinase Cepsilon interacts with cytochrome c oxidase subunit IV and enhances cytochrome c oxidase activity in neonatal cardiac myocyte preconditioning", Biochem. J., 393:191-9 (2006).

Palmer, et al., "Biochemical properties of subsarcolemmal and interfibrillar mitochondria isolated from rat cardiac muscle", J. Biol. Chem., 252: 8731-9 (1977).

Pierce and Dhalla, "Heart mitochondrial function in chronic experimental diabetes in rats", Can. J. Cardiol., 1:48-54 (1985).

Savabi, "Mitochondrial creatine phosphokinase deficiency in diabetic rat heart", Biochem. Biophys. Res. Comm., 154:469-75 (1988).

Schechtman, et al., "Glutathione S-transferase pull-down assay", Meth. Mol. Biol., 233:345-50 (2003).

Schwarze, et al., "In vivo protein transduction: delivery of a biologically active protein into the mouse", Science, 285:1569-72 (1999).

Seager, et al., "Cardiac cell damage: a primary myocardial disease in streptozotocin-induced chronic diabetes", Br. J. Exp. Pathol., 65: 613-23 (1984).

Shin, "Down-regulation of mitochondrial F1F0-ATP synthase in human colon cancer cells with induced 5-fluorouracil resistance", Cancer Res., 65(8):3162-70 (2005).

Tanaka, et al., "Mitochondrial dysfunction observed in situ in cardiomyocytes of rats in experimental diabetes", Cardiovasc. Res., 26:409-14 (1992).

Yu, et al., "Differential loss of cytochrome-c oxidase subunits in ischemia-reperfusion injury: exacerbation of COI subunit loss by PKC-epsilon inhibition", Am. J. Physiol. Heart Circ. Physiol., 294:H2637-H2645 (2008).

* cited by examiner

NH2-AGRKLALKTIDWVSF-COOH (SEQ ID NO: 1)
NH2-DWVSFVEIMPQNQKAI-COOH (SEQ ID NO: 6)
NH2-NQKAIGNLKSWNETF-COOH (SEQ ID NO: 7)
NH2-WNETFHTRLASLSEKP-COOH (SEQ ID NO: 8)
NH2-LSEKPPAIDWAYYRAN-COOH (SEQ ID NO: 9)
NH2-YYRANVDKPGLVDDFK-COOH (SEQ ID NO: 10)
NH2-VDDFKNKYNALKIPVP-COOH (SEQ ID NO: 11)
NH2-KIPVPEDKYTALVDAE-COOH (SEQ ID NO: 12)
NH2-LVDAEEKEDVKNCAQF-COOH (SEQ ID NO: 13)
NH2-NCAQFVTGSQARVREY-COOH (SEQ ID NO: 14)
NH2-RVREYEKQLEKIKNMI-COOH (SEQ ID NO: 2)
NH2-IKNMIPFDQMTIDDLN-COOH (SEQ ID NO: 15)
NH2-IDDLNEVFPETKLDKR-COOH (SEQ ID NO: 16)
NH2-KLDKRKYPYWPHQPIENL-COOH (SEQ ID NO: 17)

FIG.11

Inhibitor/Antagonist
SEQ ID NO: 3

| Tat-PTD | Mitochondrial-targeting | dF₁F₀ sequence | Flag | |
|---|---|---|---|---|
| NH₂ | YGKKRRQRRR | MLATRALSLIGKRAISTSVC | AGRKLALKTIDWVSF | DYKDDDDK | COOH |
| | SEQ ID NO: 18 | SEQ ID NO: 19 | SEQ ID NO: 1 | SEQ ID NO: 20 |

Facilitator/Agonist
SEQ ID NO: 4

| | | | | |
|---|---|---|---|---|
| NH₂ | YGKKRRQRRR | MLATRALSLIGKRAISTSVC | PVREYEKQLEKIKNMI | DYKDDDDK | COOH |
| | SEQ ID NO: 18 | SEQ ID NO: 19 | SEQ ID NO: 2 | SEQ ID NO: 20 |

PEPTIDE MODULATORS OF THE δPKC INTERACTION WITH THE D SUBUNIT OF F₁FO ATP SYNTHASE/ATPASE AND USES THEREOF

CROSS REFERENCE TO RELATED APPLICATION

This is a continuation application under 35 U.S.C. §120 of pending international application PCT/US2010/002268, filed Aug. 18, 2010, which claims benefit of priority under 35 U.S.C. §119(e) of provisional U.S. Ser. No. 61/396,375 filed Jun. 18, 2010, and U.S. Ser. No. 61/274,431 filed Aug. 18, 2009, the entirety of all of which is hereby incorporated by reference.

STATEMENT REGARDING FEDERALLY SPONSORED RESEARCH OR DEVELOPMENT

This invention was made with government support under grant R01-076805 awarded by the NIH. The government has certain rights in the invention.

BACKGROUND OF THE INVENTION

1. Field of the Invention

The present invention relates to the fields of cardiology, ischemic heart disease and cardiovascular pharmacology as well as diabetes and cancer. More specifically, the present invention relates to, inter alia, peptide modulators of the "d" subunit of $F_1Fo$ ATP synthase/ATPase (d $F_1Fo$ and uses thereof.

2. Description of the Related Art

In the United States, someone dies every minute as a result of coronary artery blockage resulting in a heart attack (1). In fact, heart attacks are responsible for more annual deaths than any other single medical condition and half of those suffering a myocardial infarction (MI) will not survive the attack (1). Of those arriving at the hospital alive, 40% will die within the first year, and for those surviving past 1 year, many will develop co-morbidities such as congestive heart failure, which itself carries a 50% mortality rate at 5 years. The most common underlying cause of heart attacks involves occlusion of one or more coronary vessels by atherosclerosis or thrombi formation. This prevents the flow of blood, and consequently the supply of oxygen, nutrients, and other factors to the myocardium. If blood flow is not restored promptly, massive cell death occurs resulting in permanent cardiac injury. In diabetics, the progression of coronary artery disease is greatly accelerated and the severity of cardiac injury suffered following a heart attack is generally 3-5-times as severe as in non-diabetics of comparable age (2).

Clinical therapy for heart attack victims focuses on the rapid restoration of blood flow by thromobolysis, angioplasty, stenting and when appropriate surgical coronary artery bypass grafts (3). A majority of cardiac cell death associated with a heart attack actually occurs during the early phases of reperfusion when blood flow is restored (4). Therefore, cardioprotective agents that minimize cell death during reperfusion therapy are desperately needed and would greatly improve the outcomes of these patients.

Mammalian protein kinase C (PKC) exists as a 10 member family of closely related serine/threonine kinases, with each individual kinase being identified by a unique Greek letter designation. δPKC is a member of this large family of enzymes. PKC isozymes have been categorized into 3 subfamilies: classical ($\alpha$, $\beta_I$, $\beta_{II}$, $\gamma$), novel ($\delta$, $\epsilon$, $\eta$, $\theta$) and the atypical ($\zeta$, $\lambda$/$\iota$) PKC based on amino acid homologies and responses to various PKC activators (5). In terms of in vitro phosphotransferase activities, the classical PKCs are activated by $Ca^{2+}$, phosphatidylserine (PS), and 1,2, sn-diacylglycerol (DG). The novel PKCs are $Ca^{2+}$-independent and DG/PS-sensitive, while the atypical PKCs are insensitive to both $Ca^{2+}$ and DG. In many cases the mitochondrial lipid cardiolipin can also activate PKC isozymes (6). In general, each PKC isozyme has a regulatory domain (which contains the PKC activator binding sites and many subcellular localization domains), and a catalytic domain (which contains the ATP-binding and phosphotransferase sites).

PKC structure can be divided into 5 variable amino acid sequence regions (which differ between isozymes) and 5 conserved amino acid regions. The variable amino acid regions may play important roles in PKC isozyme-unique subcellular targeting and functions in vivo (7,8). Studies in cardiac myocytes, and many other cell types, have demonstrated that upon simultaneous activation of PKC isozymes, each enzyme can translocate to different subcellular sites (9,10). This differential targeting is thought to be mediated by PKC anchoring proteins known as Receptors for Activated C-Kinase (RACKS) (7,8). In the simplest form of this model each PKC isozyme has its own RACK and only that isozyme can bind to its' own RACK because the other PKC isozymes lack the crucial structural determinants (e.g. amino acid sequence) for binding. This provides a mechanism whereby different PKC isozymes can have isozyme-selective regulatory functions within the same cell. For example, a PKC isozyme translocating to the cell nucleus might regulate gene expression, whereas a different PKC isozyme may translocate to mitochondria to regulate energy production.

Cardiac IR injury occurs when blood flow to the heart is impaired (ischemia) and when normal blood flow is restored immediately after a heart attack (reperfusion), εPKC has cardioprotective actions against IR injury through a process known as cardiac ischemic preconditioning (PC) (16). PC is a paradoxical response whereby brief bouts of ischemia and reperfusion produce protection against a subsequent more sustained IR insult (17). The role of the PKC isozyme δPKC in cardioprotection and damage is more controversial with reports indicating it plays significant roles in both PC and IR injury. For example, Mayr et al., reported that δPKC knock-out mice demonstrated decreased glycolysis and an increased lipid metabolism, which uses more oxygen to make energy, under baseline conditions, and were unable to induce a cardiac PC response (24,25). In contrast, Mochly-Rosen and colleagues demonstrated that the activation of δPKC induces apoptosis and delays the reactivation of pyruvate dehydrogenase during IR injury which slows the re-supply of acetyl CoA to the Kreb's cycle (12,14). δPKC has also been reported to translocate to the mitochondria and interacts with the proapoptotic protein Bad to induce pathological hypertrophy and cardiac apoptosis (12).

There have been studies implicating PKC isozymes in the pathology of diabetes in heart and other tissues. The PKC activating lipid DG is elevated in diabetic myocardium (27-29) and reduction of DG levels appears to attenuate diabetic effects on the heart (29). Similarly, there have been reports of elevated cardiac PKC isozyme expression (30-32), translocation (33) and activity (34) under hyperglycemic conditions. Studies suggest that hyperglycemia-induced translocation of the $\alpha$, $\beta$, $\epsilon$, or δPKC isozymes correlates with phosphorylation of cardiac troponin I (cTnI) which may contribute to impaired diastolic relaxation and loss of myofibrillar $Ca^{2+}$ sensitivity (33,35). In addition, excessive PKC isozyme-modulation of ryanodine receptors (36-38), the Na/$Ca^{2+}$ exchanger (39), and other $Ca^{2+}$ handling proteins has been reported in diabetic myocardium. εPKC-mediated hyperphosphorylation of connexin 43 (Cx43) may contribute to Cx43 proteosomal degradation and cardiac arrhythmias in diabetic hearts (40,41). Farese et al. demonstrated that muscle-specific knock-out of ζPKC correlated with defective translocation of the GLUT4 glucose transporter to the plasma membrane and the development of insulin resistance in adipocytes (42). Finally, the βPKC isozymes have been implicated in hyperglycemia-induced hypertrophy (43), elevation of ROS (43), and diabetic cardiomyopathy (44). Therefore, an extensive literature supports a role for PKC isozymes in the cardiac pathology of diabetes, but few studies have examined mitochondrial PKC isozyme targets in diabetes. Malhotra et al. reported that transgenic over-expression of an εPKC-selective activating peptide reduced streptozotocin (STZ)-induced εPKC translocation to the plasma membrane and mitochondria, which was associated with diminished oxidative stress, ventricular dysfunction, and apoptosis (45). Arikawa et al. used oligo-nucleotide arrays to correlate up-regulation of cardiac PKC isozyme gene expression with diminished levels of pyruvate dehydrogenase kinase isoenzyme 4 (PDK4) and the mitochondrial uncoupling protein 3 (UCP3) (46). ATP levels and OXPHOS enzyme activities are reduced in diabetes (47-58).

The mammalian $F_1Fo$ ATP synthase is a 16 subunit enzyme complex. It contains an $F_1$ domain (3α, 3β, γ, δ, and ε subunits), which protrudes into the mitochondrial matrix (59-61). The interlaces between α and β subunits are the site of nucleotide binding and ATP synthesis. It also has an Fo domain, which is a proton channel that traverses the IM and allows proton re-entry into the mitochondrial matrix down a concentration gradient. This proton movement provides the energy for ATP synthesis (60,62,63,65). The $F_1$ and Fo domains are connected by a central stalk consisting of the γ, δ, and ε subunits and by a peripheral stalk, which is made up of the OSCP, F6, b, and d subunits (59-61). The central stalk is thought to rotate along with the c subunits during ATP synthesis. This rotation is crucial for proton movement through the Fo domain. The peripheral stalk acts as a stator to prevent the α and β subunits from rotating with the central stalk and c subunits. This appears to be crucial for the phosphorylation of ADP to ATP on the α and β subunits.

Following severe cardiac IR injury ATP levels decline substantially (13,64). A major component of this drop involves the loss of the electrochemical/proton gradient across the IM, which supplies the energy for ATP production by $F_1Fo$ ATP synthase. Therefore, shortly after the induction of ischemia the enzyme becomes inhibited. It then makes a futile attempt to re-establish the mitochondrial IM potential by operating in reverse to pump protons out of the mitochondrial matrix. This process is very inefficient and requires energy which is supplied by the $F_1Fo$ complex then operating in reverse-mode as an ATPase (65). If ischemia is not interrupted, $F_1Fo$ ATPase activity will contribute heavily to the loss of cardiac ATP (65). The activity of the $F_1Fo$ complex is also regulated by two endogenous inhibitors: inhibitor of $F_1$ ($IF_1$) and $Ca^{2+}$-sensitive binding-inhibitor protein (CaBl) (62, 65-69). When the enzyme is in ATPase-mode its activity is thought to be partially limited by the $IF_1$ protein.

In support of this, $IF_1$ binds $F_1Fo$ ATPase at the α and β subunit interface (65), under conditions of decreased pH and mitochondrial membrane potential (65), such as would occur in ischemia. The role of CaBl is less clear. It binds to the enzyme under low mitochondrial intracellular $Ca^{2+}$ concentration and is released from the enzyme following an increase in mitochondrial $Ca^{2+}$ concentration (68). Therefore, as $Ca^{++}$ increases in the cell to facilitate increased contractility, mitochondrial $Ca^{++}$ also increases. This relieves the inhibition of $F_1Fo$ ATP synthase by CaBl to allow more ATP synthesis as necessary for the increased cardiac contractility. Presumably its inhibition would be relieved during IR injury also, since calcium overload of cardiac myocyte mitochondria occurs in IR injury. It is generally agreed however, that changes in mitochondrial inner membrane potential and $IF_1$- and CaBl-mediated inhibition of $F_1Fo$ activities cannot completely account for the regulation of the $F_1Fo$ enzyme complex. In addition to the $F_1Fo$ ATPase-mediated ATP hydrolysis in cardiac IR injury, the return of aerobic ATP synthesis is also impaired (13,65) and the heart attempts to compensate by utilization of glucose as a preferred substrate (instead of predominately fatty acids) in anaerobic glycolysis (65). Anaerobic ATP production is not sufficient to satisfy the intense cardiac energy demands required to support contractility indefinitely and other functions. It also generates lactic acid with consequent lactic acidosis, which further damages the heart and inhibits/impairs glycolytic enzymes themselves (65). Therefore, enhancing the return of aerobic ATP production following cardiac IR would improve the survival and functionality of the heart.

Diabetes induces both structural and functional changes in cardiac mitochondria including significant loss of proteins involved in OXPHOS (47-55). There are also losses in mitochondrial DNA, $Ca^{2+}$ uptake, creatinine phospho-kinase (CPK), and ATP synthase activities (37,50,54-57) which translate into lower myocardial ATP levels. The healthy, non-diabetic heart generates ATP mostly from oxidation of fatty acids (FA) (~70%) and to a lesser extent from glucose (25%), lactate and other sources (5%) (58). In hyperglycemic states such as diabetes, excessive amounts of free FA are liberated and there is an even greater reliance on FA and a reduced utilization of glucose for cardiac energy (47,50). This increase in FA levels induces peroxisome proliferator-activated receptors (PPARs) and their cofactor peroxisome proliferator-activated receptor cofactor 1-α(PGC1-α) to enhance the transcription of genes coding for proteins involved in virtually all aspects of FA utilization (50). This leads to greater β-oxidation of long chain FA and an increase in electrons (NADH and $FADH_2$) entering the electron transport chain (ETC). However, decreased levels of OXPHOS proteins could contribute to a greater frequency of electron leak from ETC complexes and contribute to a chronic increase in ROS production, which can cause oxidative damage to proteins, lipids, and nucleic acids producing further damage in diabetes.

The yield of ATP per oxygen atom consumed indicates that oxidation of FA requires more oxygen than glucose oxidation, which may contribute to decreased cardiac efficiency in diabetic hearts. One mechanism promoting this inefficiency is the progressive FA-induced uncoupling of respiration by a family of proton translocases in the IM known as mitochondrial uncoupling proteins (UCPs). Cardiac expression of UCP2 and UCP3 is thought to be up-regulated by elevated levels of FA (49,52,58,70) and UPC expression appears to be induced by elevation of superoxide (71). Enhanced UCP expression is thought to uncouple respiration by disrupting membrane potential through proton leakage across the IM. In addition, there may be other proteins which uncouple respiration under diabetic states such as the adenine nucleotide transporter in the IM (72). This indicates that there is a lower ATP/oxygen ratio in diabetic hearts. Interestingly, studies by Boudina et al. demonstrated that increased UCP activity resulted in mitochondrial uncoupling in db/db diabetic mice (73). When compared to wild type mice, db/db mice showed increased respiration in the presence of oligomycin, decreased ATP production, and decreased ATP/oxygen ratios. An increased respiration in the presence of oligomycin would favor superoxide generation from the ETC. This is interesting in the context of these results because inhibition of $F_1Fo$ ATP synthase via the δPKC-$dF_1Fo$ interaction may also increase mitochondrial ROS production. In addition, δPKC has been reported to be a major player in cardiac IR injury and has been shown to elevate mitochondrial ROS production and induce apoptosis (15, 74-76). δPKC may therefore contribute to the exacerbation of cardiac injury in diabetes by chronically reducing ATP levels via a previously uncharacterized inhibition of the $F_1Fo$ ATP synthase complex.

Thus, there is a continued need in the art for identification of compositions and methods for treating, among other things, ischemia/reperfusion disorders. The present invention fulfills this long-standing need and desire in the art.

SUMMARY OF THE INVENTION

The present invention discloses the use of peptides derived from the "d" subunit of the mammalian mitochondrial enzyme $F_1Fo$ ATP synthase in the treatment of human disease. One of these peptides relieves a potent inhibitory effect on $F_1Fo$ activity which is mediated by delta protein kinase C (δPKC). A second peptide derived from the "d" subunit of $F_1Fo$ ATP synthase ($dF_1Fo$) enhances δPKC-mediated inhibition of $F_1Fo$ activity. Thus, the present invention discloses the use of $dF_1Fo$-derived peptides to interfere with or enhance δPKC modulation of $F_1Fo$ ATP synthase or ATPase activities. These peptides are useful in the therapy of cardiac injury from ischemic/reperfusion (IR) and hyperglycemia. One important event contributing to cardiac injury during reperfusion therapy is an excessive inhibition of the $F_1Fo$ ATP synthase by δPKC. The peptides described herein are useful to protect the myocardium by facilitating a more rapid return of aerobic ATP synthesis following an IR or hyperglycemic insult. These drugs also could be used as solo or adjunctive therapy with other cardio-protective drugs.

Thus, the present invention is directed to an isolated or synthetic peptide, comprising an amino acid sequence having at least 75% sequence identity to SEQ ID NO: 1.

In another embodiment, the present invention provides a pharmaceutical composition, comprising the isolated peptide of the present invention and a pharmaceutically acceptable carrier.

In yet another embodiment, the present invention provides a method to improve tissue survival or to prevent or reduce ischemic tissue damage or necrosis in an individual in need of such treatment, comprising the step of administering an effective dose of the composition of the present invention to said individual.

In yet another embodiment, the present invention provides a method to improve tissue survival or to prevent or reduce ischemic tissue damage, apoptosis, autophagy, or necrosis in an individual in need of such treatment, comprising the step of administering an effective dose of a composition that decreases or enhances the interaction of δPKC with the "d" subunit of the mammalian mitochondrial enzyme $F_1Fo$ ATP synthase, which leads to the inhibition of F1Fo ATP synthase or ATPase activity.

In yet another embodiment, the present invention provides one or more isolated synthetic peptides, comprising an amino acid sequence having at least 75, sequence identity to SEQ ID NO: 2.

Other and further aspects, features and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions and certain embodiments of the invention briefly summarized above are illustrated in the appended drawings. These drawings form a part of the specification. It is to be noted, however, that the appended drawings illustrate preferred embodiments of the invention and therefore are not to be considered limiting in their scope.

FIG. 1A, representative autoradiographs for each PKC isozyme are shown. FIG. 1B, mean±S.E. densitometry values for three independent myocyte preparations. Asterisks indicate significant differences between 4-α PMA and 3 nM or 100 nM 4-β PMA ($p<0.05$). # indicates statistically significant differences between 3 and 100 nM 4-β PMA ($p<0.05$).

FIG. 3A, representative autoradiographs for each PKC isozyme are shown. FIG. 3B, mean±S.E. densitometry values for 4 independent experiments, each conducted on a separate myocyte preparation. The asterisk indicates statistically different from the Nx group ($p<0.0002$).

and phosphatidylserine (PS). Data shown represent mean±S.E. values from 3 independent experiments.

Figure 6A:
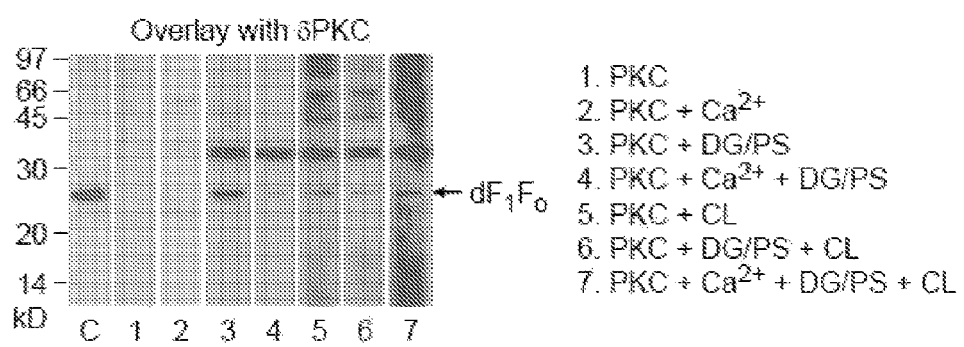
Figure 6B:
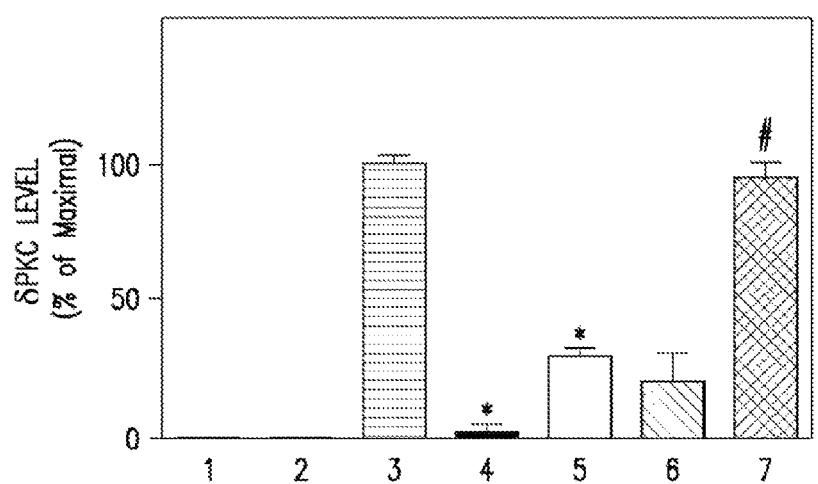

FIGS. 6A-6B: δPKC directly binds to the "d" subunit of $F_1Fo$ ATPase ($dF_1Fo$) in overlay assays. Purified $F_1Fo$ ATPase (79) was subjected to SDS-PAGE to resolve individual subunits and transferred to nitrocellulose paper (NCP) followed by Western blot analyses using $dF_1Fo$ antisera (lane C, FIG. 6A) or PKC overlay binding assay (lanes 1-7). Briefly, the NCP strips were overlaid with a mixture of purified PKC isozymes and then the overlay strips were probed for δPKC under various conditions (lane 1, PKC; lane 2, PKC+$Ca^{++}$; lane 3, PKC+diacylglycerol (DG)/phosphatidylserine (PS); lane 4 PKC+$Ca^{++}$+DG/PS; lane 5, PKC cardiolipin (CL) (note that CL is an important mitochondrial lipid and also an activator of most PKC isozymes); lane 6, PKC+DG/PS+CL; lane 7, PKC+$Ca^{++}$+DG/PS CL. Representative autoradiographs for the δPKC isozyme binding are shown in FIG. 6A and the histogram in FIG. 6B represents mean±S.E. values from 3 independent experiments. *, lane 4 or 5 vs. 3 ($p<0.0003$); lane 6 vs. 7 ($p<0.003$).

Figure 7A:
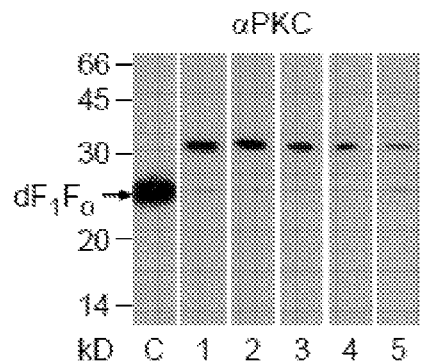
Figure 7B:
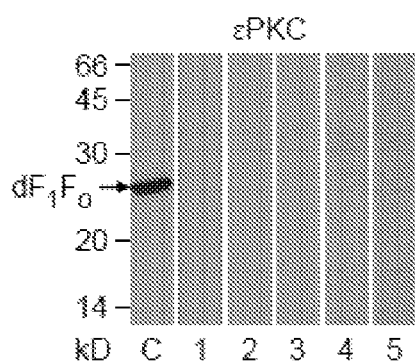
Figure 7C:
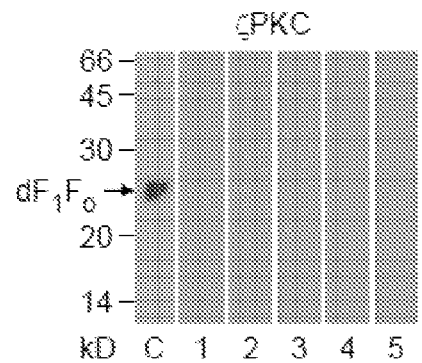
Figure 7D:
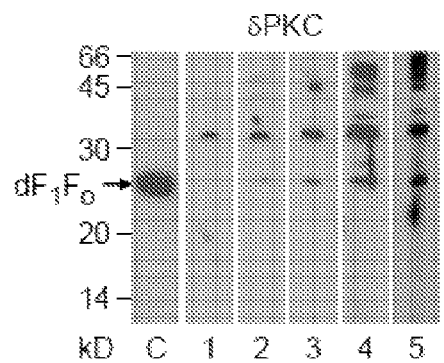

FIGS. 7A-7E: δPKC binds selectively to the "d" subunit of $F_1Fo$ ATPase ($dF_1Fo$) in a CL-dependent manner. The purified $F_1Fo$ ATPase holo-enzyme was subjected to SDS-PAGE and transferred onto nitrocellulose paper, followed by Western blot analyses using $dF_1Fo$ antisera (lane C) or overlay binding assay as in FIG. 6A (lanes 1-5). The overlay binding assay was conducted using increasing concentrations of CL (lane1, 0 μM; lane 2, 30 μM; lane 3, 100 μM; lane 4, 300 μM; and lane 5, 1 μM). The overlay strips were then probed for αPKC (FIG. 7A), εPKC (FIG. 7B), ζPKC (FIG. 7C) and δPKC (FIG. 7D). Representative autoradiographs for each PKC isozyme are shown, and the histogram (FIG. 7E) represents mean±S.E. values from 3 independent experiments showing δPKC binding to $dF_1Fo$. * indicates significantly significant differences between 300 μM or 1000 μM when compared to 30 μM CL groups. Comparisons were made (to 30 μM group) because there was no detectable densitometry values (binding) in the 0 μM (control) groups.

Figure 8A:
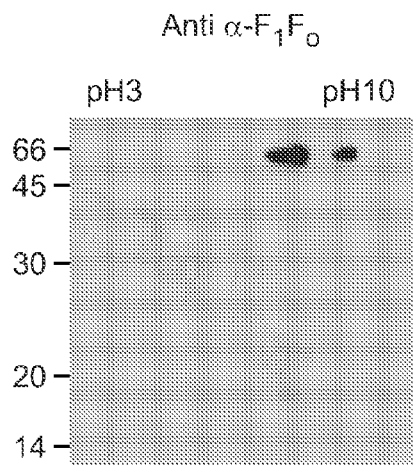
Figure 8B:
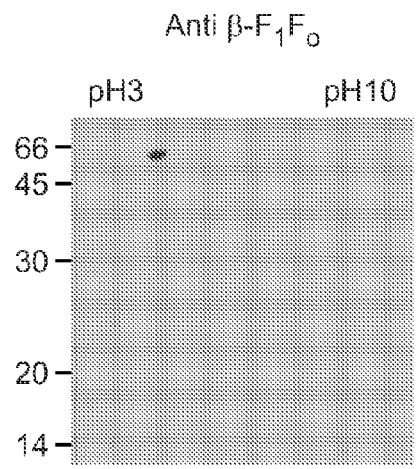
Figure 8C:
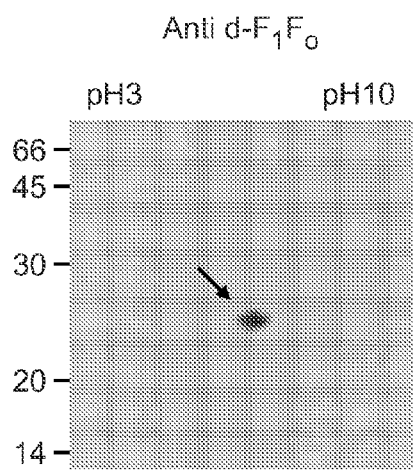
Figure 8D:
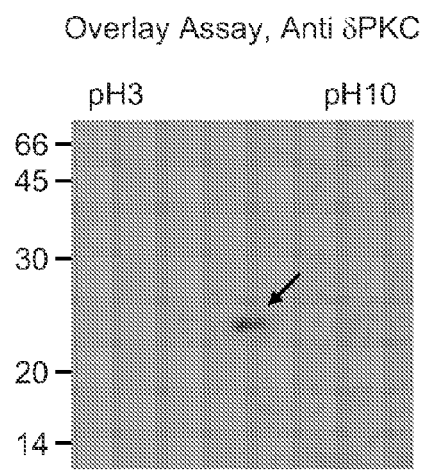

FIGS. 8A-8D: δPKC binds to the "d" subunit of $F_1Fo$ ATPase ($dF_1Fo$) in two-dimensional electrophoresis overlay assays. The purified $F_1Fo$ ATPase holo-enzyme was separated using pH 3-10 NL IPG strips followed by SDS-PAGE to resolve individual subunits and transferred onto nitrocellulose paper, followed by Western blot analyses using antisera against the $F_1Fo$ ATPase α (FIG. 8A), ATPase β (FIG. 8B), and ATPase d (FIG. 8C) subunits. FIG. 8D is a PKC overlay experiment conducted on a two-dimensional blot of $F_1Fo$ subunits, and the overlaid blot was probed for δPKC. Representative autoradiographs for each antisera are shown (FIGS. 8A-8O) from 3 independent experiments.

Figure 9A:
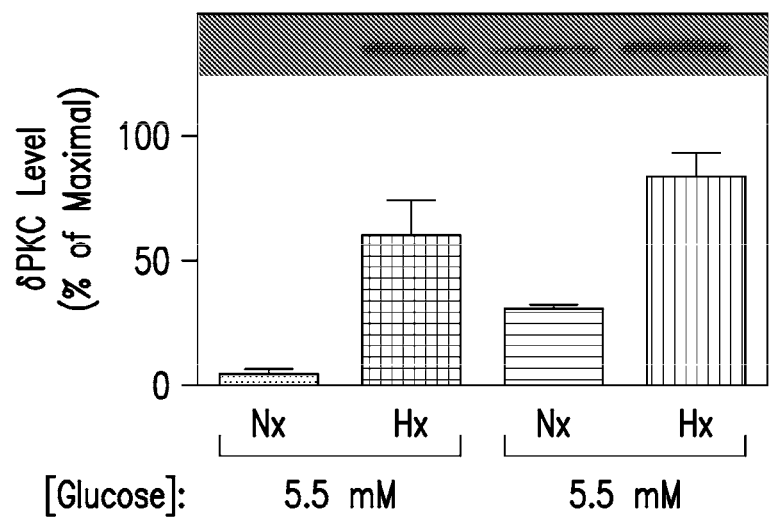
Figure 9B:
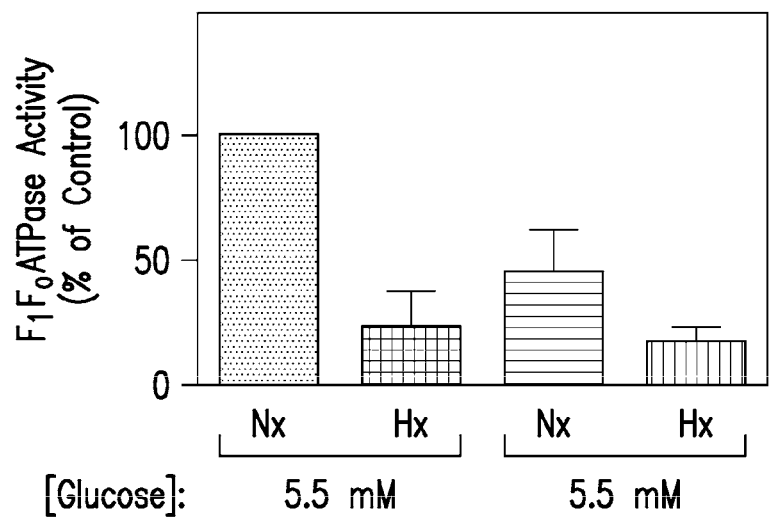

FIGS. 9A-9B: High glucose induces the δPKC-$dF_1Fo$ co-immunoprecipitation (co-IP) and inhibition of $F_1Fo$ ATPase activity in neonatal cardiac myocytes (NCMs) under normoxic (Nx) and hypoxic (Hx) conditions. Cells were cultured for 24 hr under normal (5.5 mM) or high glucose conditions. Next cells were exposed to a 4 hr incubation under Nx or Hx conditions in an anaerobic chamber. Mitochondria were then isolated using Percoll Optiprep density gradients and subjected to δPKC-$dF_1Fo$ co-IP analyses (FIG. 9A) as in FIG. 3 or $F_1Fo$ ATPase activity assays (FIG. 9B) as in FIG. 4. The top portion of FIG. 9A is a representative autoradiograph taken from a single experiment. Histograms represent mean±S.E. values from 4 independent experiments.

FIGS. 10A-10E: Myocardium from rats subjected to streptozotocin-induced diabetes demonstrate induction of the δPKC-$dF_1Fo$ co-immunoprecipitation (co-IP), inhibition of $F_1Fo$ ATPase activity and decreased ATP levels. Sprague-Dawley rats (~2 months old/250 g) were administered streptozotocin (50 mg/kg) by tail vein injection and diabetic phenotype was allowed to develop for an additional 6 weeks. Hyperglycemia was confirmed by blood glucose monitoring. Hearts were then removed and used in Langendorff preparations given normoxic incubations (Con) or administered a 20 min global no-flow ischemia followed by a 90 min oxygenated reperfusion period. Hearts were then quickly harvested and mitochondria were isolated from the left ventricle using Percoll/Optiprep density gradients. Mitochondria isolated via this technique are >90% intact in each treatment group. Mitochondria were then homogenized in isotonic buffer and subjected to Western blots for total δPKC levels (FIG. 10A), $dF_1Fo$ levels (FIG. 10B) or were used in δPKC-$dF_1Fo$ co-IP (FIG. 10C), $F_1Fo$ ATPase (FIG. 10D), or tissue ATP level (FIG. 10E) assays. Results shown in histograms are mean±S.E. values and represent 3 animals per treatment group.

FIG. 11: Description of sequential peptides derived from the "d" subunit of adult rat $F_1Fo$ ATP synthase ($dF_1Fo$). Shown are the amino acid sequences of the 14 peptides used to determine their effects on δPKC binding to $dF_1Fo$. Peptides are listed in order beginning with the N-terminus of $dF_1Fo$ in peptide 1 and ending with the COOH-terminal $dF_1Fo$ sequence in peptide 14. Each peptide contains a 5 amino acid overlap with the previous sequential peptide. Also note that the N-terminal methionine has been deleted from peptide 1 because it is not thought to be present in the mature $dF_1Fo$ protein. Other modifications to certain amino acid side chains of the peptides were made to better mimic their in vivo chemistry. Amino acids are indicated by universally accepted single letter abbreviations.

Figure 12A:
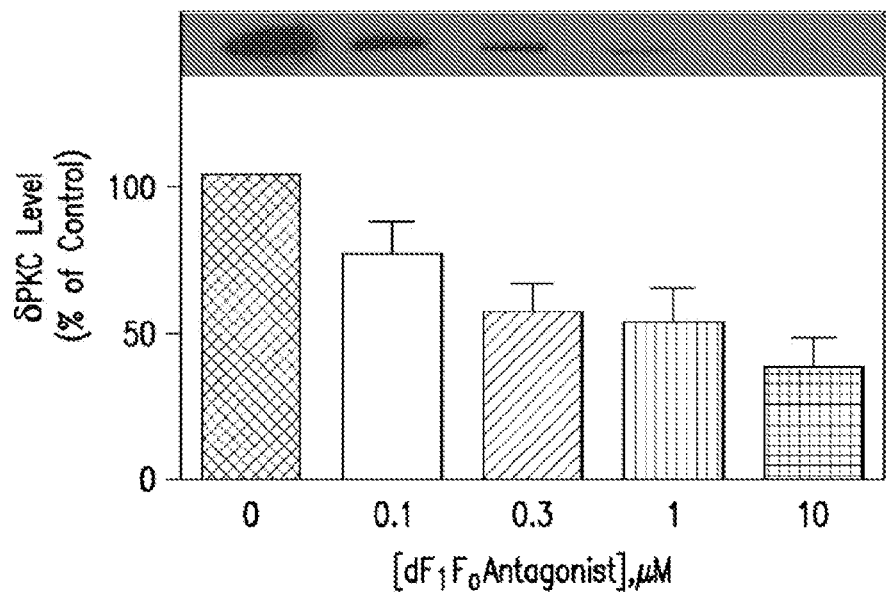
Figure 12B:
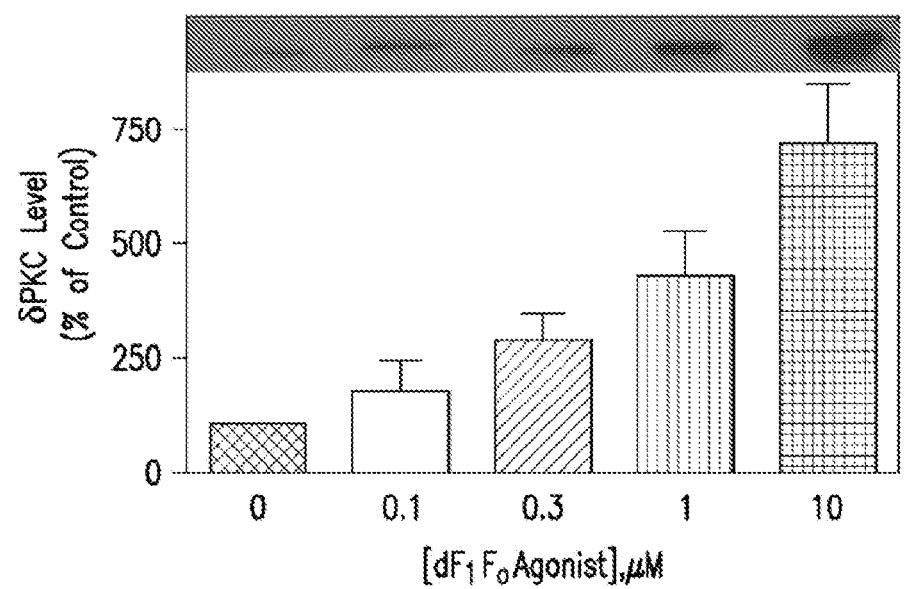

FIGS. 12A-12B: Modulation of δPKC binding to the d subunit of $F_1Fo$ ATP synthase ($dF_1Fo$) by $dF_1Fo$-derived peptides. Peptides contain the putative δPKC-$dF_1Fo$ inhibitor, facilitator or scrambled (inactive) amino acid sequences, an HIV-Tat protein transducing (PTD) sequence (YGRKKRRQRRR; SEQ ID NO: 18) for cell uptake, a mitochondrial targeting sequence (MLATRALSLIGKRAIST-SVC; SEQ ID NO: 19) and a Flag epitope (DYKDDDDK; SEQ ID NO: 20). B and C) PKC overlay assays revealing an inhibitor (FIG. 12A) and a facilitator (FIG. 12B) of the δPKC-$dF_1Fo$ binding interaction. Purified $F_1Fo$ ATPase holo-enzyme (79) was subjected to SDS-PAGE to resolve individual subunits and transferred onto nitrocellulose paper (NCP), NCP strips were "overlayed" with a mixture of purified PKC isozymes (40) in the presence of PKC activators (diacylglycerol and phosphatidylserine) and 0-10 mM concentrations of the putative δPKC-$dF_1Fo$ inhibitor or facilitator, followed by Western blot analyses using δPKC-selective antisera. Representative autoradiographs are shown and the histogram values represent mean±S.E. % of "no peptide control" densitometry values from 9 independent experiments for FIGS. 12A and 6 experiments for FIG. 12B.

FIG. 13: Amino acid sequences of cell-permeable, mitochondrial-targeted scrambled-sequence inactive control, inhibitor (antagonist) and facilitator (agonist) peptides. Peptides contain the putative δPKC-$dF_1Fo$ inhibitor, facilitator, or scrambled (inactive) sequences, an HIV-Tat protein transducing (PTD) sequence (YGRKKRRQRRR) for cell uptake, a mitochondrial targeting sequence (MLATRALS-LIGKRAISTSVC) and a Flag epitope (DYKDDDDK). The Tat-PTD sequence is conjugated to the mitochondrial targeting sequence by a cysteine-cysteine disulfide bond (88).

Figure 14:
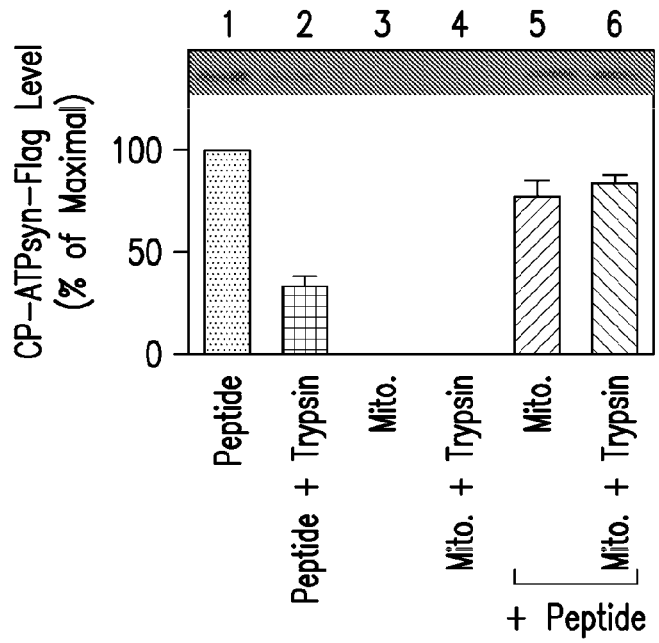

FIG. 14: Exposure of neonatal rat cardiac myocytes (NCMs) to the HIV Tat-coupled, mitochondrial-targeted version of the δPKC-$dF_1Fo$ inhibitor leads to uptake into gradient-purified mitochondria. The δPKC-dF₁Fo inhibitor was incubated in the absence (lane 1) or presence (lane 2) of 100 Units/ml of trypsin for 20 minutes at 4° C. and then subjected to SDS-PAGE, followed by Western blot analysis using anti-Flag antisera. NCMs were also treated in the absence (lanes 3-4) or presence (lanes 5-6) of 100 nM extracellular concentrations of the δPKC-dF₁Fo inhibitor for 2 hrs. Mitochondria were then purified using Percoll Optiprep density gradient techniques. Isolated mitochondria were then subjected to SDS-PAGE and Western blot analysis using antisera directed against the Flag epitope. These mitochondria were incubated in the absence (lane 5) and presence (lane 6) of 100 Units/ml of trypsin for 20 minutes at 4° C. immediately after isolation. Representative autoradiographs for Flag immunoreactivity are shown and histograms represent mean±S.E. % of maximal densitometry values from 3 independent experiments.

Figure 15A:
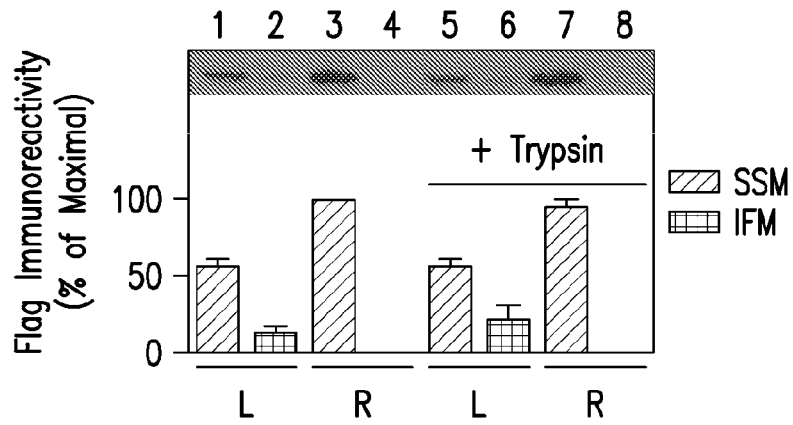
Figure 15B:
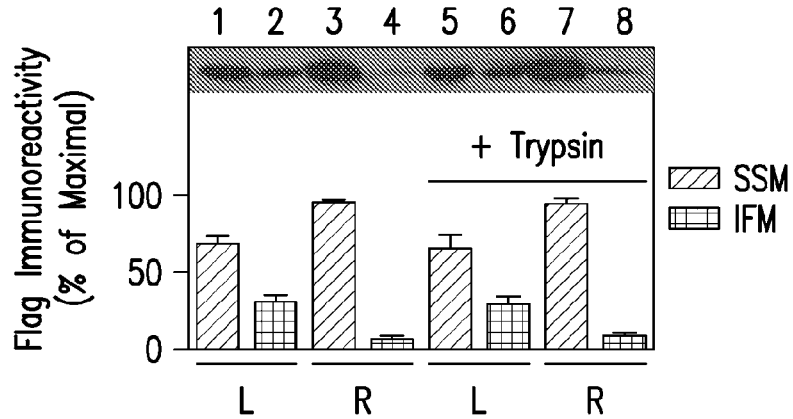

FIGS. 15A-15B: Addition of HIV-Tat protein transduction and mitochondrial targeting sequences to the δPKC-dF₁Fo modulatory peptides promotes mitochondrial uptake in perfused rat hearts. The Cell-permeable, mitochondrial targeted δPKC-dF₁Fo inhibitor was prepared as previously described in our publications. Next isolated rat hearts were equilibrated to attain stable contractile parameters, and then perfused for 20 (FIG. 15A) or 60 (FIG. 15B) min with 20 nM concentrations of the δPKC-dF₁Fo inhibitor (B) peptide. Hearts were rapidly excised and left (L) and right (R) ventricles isolated. Subsarcolemmal (SSM) and interfibrillar (IFM) mitochondria were then isolated using Percoll/Optiprep density gradients. In lanes 1-4 of FIGS. 15A-15B, 50 μg of SSM or IFM from each ventricle, was subjected to SDSPAGE and Western blot analysis with anti-Flag antisera (recall that the δPKC-dF₁Fo inhibitor has a Flag epitope tagging sequence engineered into its N-terminus). In lanes 5-8 of FIGS. 15A-15B, SSM and IFM isolated from hearts perfused with the δPKC-dF₁Fo modulatory peptide was first incubated with trypsin to proteolyze any peptide adhering to extra-mitochondrial surfaces. Samples were then subjected to SDSPAGE and Western blot analysis with anti-Flag antisera. Note that trypsinization of SSM and IFM did not alter anti-Flag immunoreactivity indicating that the δPKC-dF₁Fo inhibitor entered SSM and IFM when perfused into isolated rat hearts. Typical autoradiographs are shown in the top portion of each of FIGS. 15A-15B. Histograms represent mean+S.E. densitometry data from 5 independent analyses each conducted using a separate perfused heart.

Figure 16:
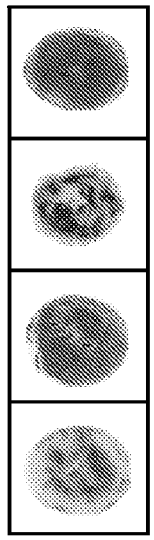

FIG. 16: The δPKC-dF₁Fo interaction inhibitor and facilitator peptides have opposite effects on ischemia/reperfusion injury in isolated rat hearts. Hearts were excised from 2 month-old Sprague-Dawley rats and subjected to Langendorff-mode perfusion with oxygenated Kreb's buffer. Following a 20 min equilibration to attain stable beating hearts either were perfused continuously for 110 minutes (Con) or were subjected to 20 minutes of global no-flow ischemia and then 90 minutes of oxygenated reperfusion (IR). For groups receiving the δPKC-dF₁Fo inhibitor or facilitator peptides (complete amino acid sequences shown in FIG. 13) 20 nM concentrations of the peptides were given at the onset of the 90 minute reperfusion period for 20 minutes. At the termination of experimentation atria were removed and ventricles were rapidly washed in chilled Kreb's buffer and partially frozen to facilitate cutting the hearts into sections. Sections were then stained using standard triphenyl-tetrazolium chloride techniques (infarcted areas appear light, live areas appear dark). Representative sections are shown and Mean±S.E. infarct sizes are plotted in FIG. 17. Note that the δPKC-dF₁Fo inhibitor (antagonist) protected against infarction (darker) and the δPKC-dF₁Fo facilitator (agonist) exacerbated infarction in this model.

Figure 17:
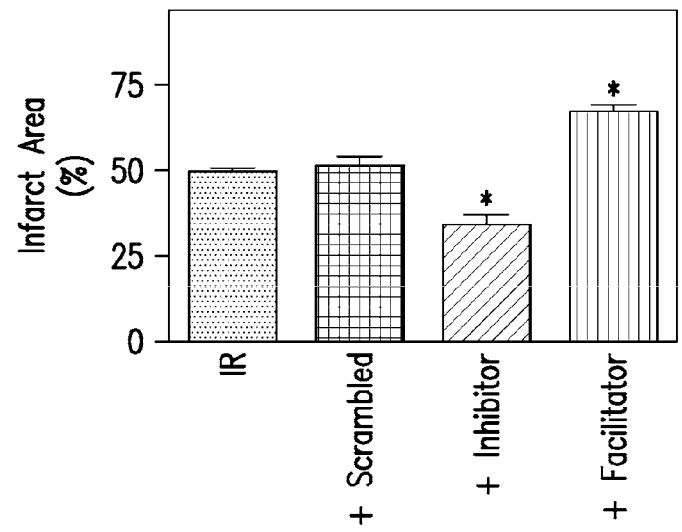

FIG. 17: Quantitation of the infarct-sparing and infarct-worsening effects of the δPKC-dF₁Fo modulatory peptides using triphenyltetrazoliumn techniques. Experiments were the same as those conducted as in FIG. 16. Histograms represent mean±S.E. infarction expressed as a percentage of the entire left ventricular area. Each treatment group included 5 rats except for the facilitator peptide which included 3 animals.

Figure 18:
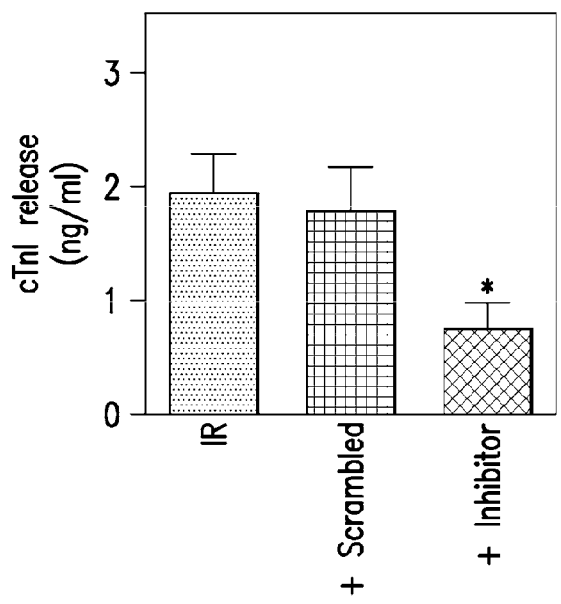

FIG. 18: Quantitation of the infarct-sparing effects of the δPKC-dF₁Fo inhibitor peptide using serum levels of cardiac troponin I (cTnI). Quantitation of cTnI release was monitored from the same isolated heart preparations used in FIGS. 16-17. cTnI was detected by a rat-specific ELISA kit according to manufacturers instructions. Data are plotted as mean±S.E cTnI values in eluates from 5 rat hearts in each group.

DETAILED DESCRIPTION OF THE INVENTION

As used herein, the term "a" or "an", when used in conjunction with the term "comprising" in the claims and/or the specification, may refer to "one", but it is also consistent with the meaning of "one or more", "at least one", and "one or more than one". Some embodiments of the invention may consist of or consist essentially of one or more elements, method steps, and/or methods of the invention. It is contemplated that any device or method described herein can be implemented with respect to any other device or method described herein. As used herein, the term "or" in the claims refers to "and/or" (unless explicitly indicated to refer to alternatives only or the alternatives are mutually exclusive, although the disclosure supports a definition that refers to only alternatives and "and/or". As used herein, the term "contacting" refers to any suitable method of bringing a compound or a composition into contact with a cell. In vitro or ex vivo this is achieved by exposing the cell to the compound or agent in a suitable medium. For in vivo applications, any known method of administration is suitable as described herein. As used herein, the term "subject" refers to any human or non-human recipient of the composition described herein.

The present invention is directed to an isolated or synthetic peptide, comprising an amino acid sequence having at least 75% sequence identity to SEQ ID NO: 1. In addition, the present invention encompasses a peptide which comprises an amino acid sequence having at least 85% sequence identity to SEQ ID NO: 1, a peptide which comprises an amino acid sequence having at least 90% sequence identity to SEQ ID NO: 1, a peptide which comprises an amino acid sequence having at least 95% sequence identity to SEQ ID NO: 1 or a peptide which comprises an amino acid sequence having at least 100% sequence identity to SEQ ID NO: 1.

It is also contemplated that the peptides of the present invention may be further modified to have a modification selected from the group consisting of addition of a detectable label, glycosylation, hydroxylation, alkylation, methylation, sulfation, reduction, calcium depletion, calcium supplementation, conjugation, and addition of a group or moiety to improve stability of the peptide, addition of a group or moiety to improve bioavailability of the peptide, addition of a group or moiety to improve cell permeability of the peptide or both stability and bioavailability of the peptide or addition of a group or moiety to improve mitochondrial uptake of the peptide. A representative example of a group or moiety to improve cell permeability of the peptide includes but is not limited to the human immunodeficiency virus (HIV) Tat protein transduction domain (SEQ ID NO: 18). A representative example of a group or moiety to improve mitochondrial uptake of the peptide is a mitochondrial targeting sequence such as, but not limited to, that found in the number IV subunit of cytochrome oxidase (SEQ ID NO: 19).

The present invention is directed to an isolated nucleic acid molecule encoding the peptide or peptide backbone described herein.

The present invention is further directed to a pharmaceutical composition, comprising the isolated peptides described herein, and a pharmaceutically acceptable carrier. The pharmaceutical composition of the present invention may be formulated to improve stability of the peptide, bioavailability of the peptide, or both stability and bioavailability of the peptide. In addition, the pharmaceutical composition may further comprise a hemostatic compound, an antimicrobial compound, an antibacterial compound, or any combination thereof.

The present invention is further directed to a kit comprising the peptides of the present invention.

The present invention is further directed to a method to improve tissue survival or to prevent or reduce ischemic tissue damage, apoptosis, autophagy, or necrosis in an individual in need of such treatment, comprising the step of administering an effective dose of the composition of the present invention to said individual.

The present invention is further directed to a method to improve tissue survival or to prevent or reduce ischemic tissue damage, apoptosis, autophagy, or necrosis in an individual in need of such treatment, comprising the step of administering an effective dose of a composition that decreases the interaction of δPKC with the "d" subunit of the mammalian mitochondrial enzyme $F_1Fo$ ATP synthase and the consequent inhibition of $F_1Fo$ ATP synthase or ATPase activity. In one preferred embodiment, the composition is the pharmaceutical composition described herein. It is contemplated that this method would be useful in treating a variety of conditions, including but not limited to diabetes, atherosclerotic vascular disease or age-related vasculopathy, stroke, post-myocardial infarctions, hypertension, inflammation, or anaphylactic shock and cancer.

The present invention is further directed to an isolated or synthetic peptide, comprising an amino acid sequence having at least 75% sequence identity to SEQ ID NO: 2. In addition, the present invention encompasses a peptide which comprises an amino acid sequence having at least 85% sequence identity to SEQ ID NO: 2, a peptide which comprises an amino acid sequence having at least 90% sequence identity to SEQ ID NO: 2, a peptide which comprises an amino acid sequence having at least 95% sequence identity to SEQ ID NO: 2 or a peptide which comprises an amino acid sequence having at least 100% sequence identity to SEQ ID NO: 2. These peptides may be further modified to have a modification selected from the group consisting of addition of a detectable label, glycosylation, hydroxylation, alkylation, methylation, sulfation, reduction, calcium depletion, calcium supplementation, conjugation, and addition of a group or moiety to improve stability of the peptide, addition of a group or moiety to improve bioavailability or targeting of the peptide, addition of a group or moiety to improve cell permeability of the peptide or both stability and bioavailability of the peptide or addition of a group or moiety to improve mitochondrial uptake of the peptide. A representative example of a group or moiety to improve cell permeability of the peptide includes but is not limited to the human immunodeficiency virus (HIV) Tat protein transduction domain. A representative example of a group or moiety to improve mitochondrial uptake of the peptide is a mitochondrial targeting sequence such as, but not limited to, that found in the number IV subunit of cytochrome oxidase. Also provided are an isolated nucleic acid molecule encoding the peptide or peptide backbone shown in SEQ ID NO: 2, a pharmaceutical composition, comprising the isolated peptide shown in SEQ ID NO: 2 and a pharmaceutically acceptable carrier, including such a pharmaceutical composition formulated to improve stability of the peptide, bioavailability of the peptide, or both stability and bioavailability of the peptide as well as a kit comprising a peptide shown in SEQ ID NO: 2.

The following example(s) are given for the purpose of illustrating various embodiments of the invention and are not meant to limit the present invention in any fashion.

Figure 1A:
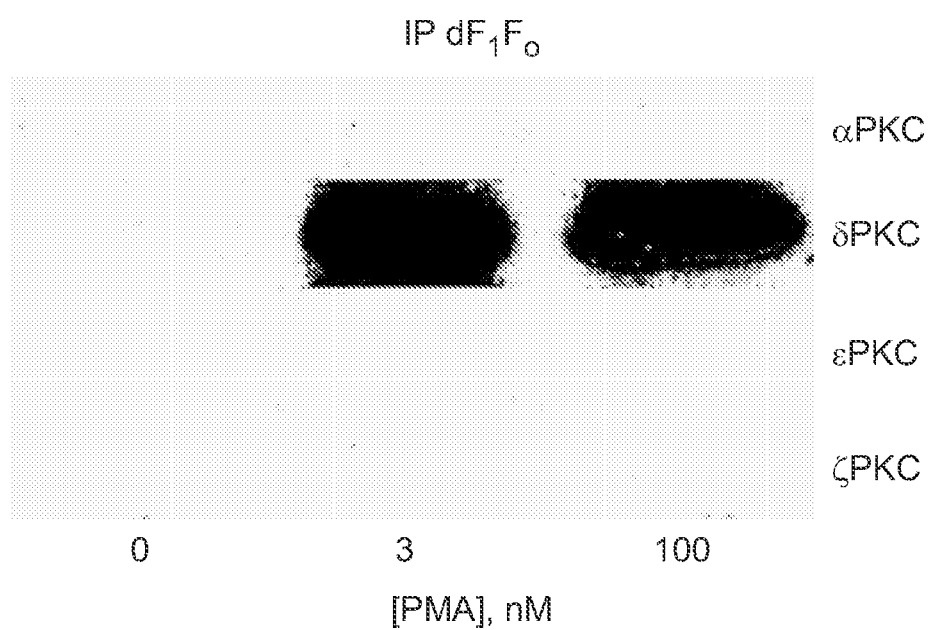
FIGS. 1A-1B: Delta protein kinase C (δPKC) co-immunoprecipitates (co-IPs) with the "d" subunit of $F_1Fo$ ATP synthase ($dF_1Fo$) following 100 nM 4-β PMA treatment. Neonatal cardiac myocytes (NCMs) were treated with 100 nM 4-α PMA (0 nM in Figure), 3 nM 4-β PMA for 1 hr. or 100 nM 4-β PMA for 20 min. Mitochondria were isolated using Percoll/Optiprep density gradients and then subjected to immunoprecipitations using antisera to $dF_1Fo$. IPs were resolved by SOS-PAGE and transferred onto nitrocellulose paper (NCP) followed by Western blot analyses using antisera against αPKC, δPKC, εPKC and ζPKC.
Figure 1B:
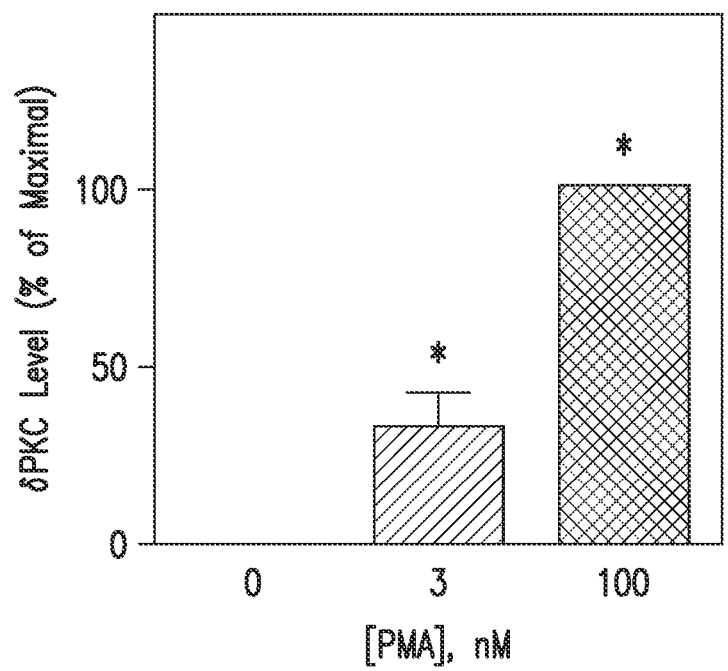

EXAMPLE 1

δPKC Co-Immunoprecipitates with the "d" Subunit of the $F_1Fo$ ATPase ($dF_1Fo$) Following Treatment of Neonatal Cardiac Myocytes (NCMs) with Phorbol Ester Phorbol esters such as 4-β phorbol 12-myristate-13-acetate (4-β PMA), are well known activators of most PKC isozymes and should be useful in determining if one or more PKC isozymes induced effects on the $F_1Fo$ complex. In FIG. 1 (F5) NCMs were treated with 3 or 100 nM 4-α (inactive isomer) and 4-β PMA (active isomer), mitochondria were isolated and solublized and then subjected to immunoprecipitation (IP) using antisera against the "d" subunit of $F_1Fo$ ATP synthase ($dF_1Fo$). In FIG. 1, 4-α PMA is shown as "0" concentration and 413 PMA values are reported for 3-100 nM concentrations. IPs were next subjected to Western blot analyses with anti-PKC isozyme-selective antisera. The predominant PKC isozymes found in (NCM) mitochondrial are the α, δ, ε and ζPKC isozymes. Following exposure of NCMs to 100 nM 4-β PMA the δPKC isozyme (but not the α, ε or ζPKC isozymes) showed a robust co-IP with $δF_1Fo$. On average the $δPKC$-$dF_1Fo$ co-IP increased 3.4±0.3-fold above 3 nM 4-β PMA-induced levels after 100 nM 4-β PMA treatment. In FIG. 1 (*) indicates statistically significant differences from control and (#) indicates statistically different from 3 nM 4-β PMA group.

EXAMPLE 2

4-β PMA Treatment Inhibits $F_1Fo$ ATPase Activity in NCMs

Figure 2:
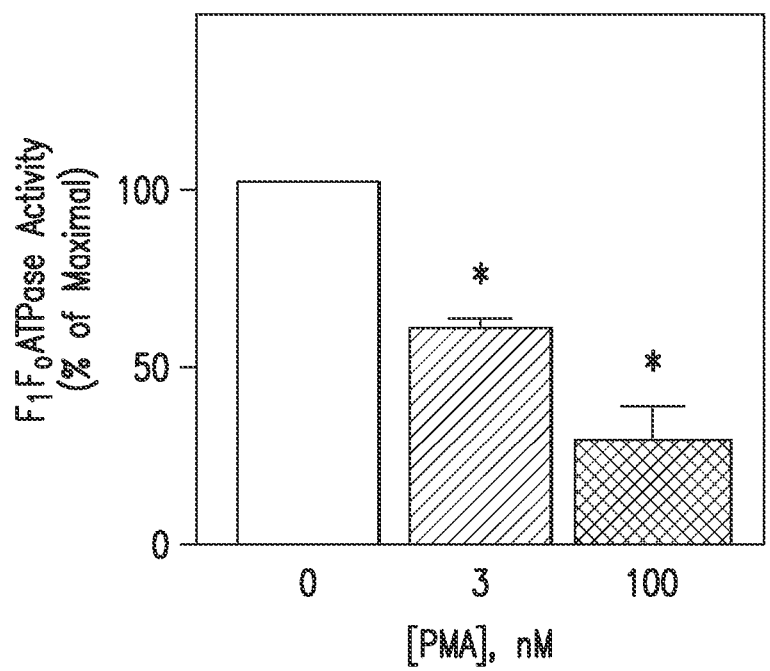
FIG. 2: 4-β PMA attenuates $F_1Fo$ ATPase activity. Neonatal cardiac myocytes (NCMs) were treated as in FIG. 1. The oligomycin-sensitive $F_1Fo$ ATPase activity was measured spectrophotometrically using sonicated NCM lysates. Results are expressed as mean±S.E. from 4 independent experiments, each conducted in triplicate, using samples from four different myocyte preparations. Asterisks indicate statistically significant differences between 4-α PMA and either 3 or 100 nM 4-β PMA ($p<0.001$).

To determine if the above $δPKC$-$dF_1Fo$ co-IP correlated with changes in $F_1Fo$ activity, mitochondria from NCMs were isolated and the $F_1Fo$ complex were solublized. Since the mitochondrial electrochemical/proton gradient is disrupted by these isolation procedures, the enzyme operates in reverse-mode as an ATPase. Therefore, $F_1Fo$ ATPase activity in these assays was monitored as an index of $F_1Fo$ complex activity. NCMs were exposed to 0, 3, or 100 nM 4-β PMA and assayed for $F_1Fo$ ATPase activity. 3 nM 4-β PMA inhibited the basal, oligomycin-sensitive $F_1Fo$ ATPase activity by 39.7±3.1%. This inhibition was increased to 72.1±9.4% following a 20 min, 100 nM 4-β PMA exposure (FIG. 2). Mean±S.E. values are plotted in FIG. 2 from 4 independent experiments, each from a separate NCM preparation. (*) denotes statistically different from 0 nM PMA group. These results demonstrated that the 4-β PMA-induced δPKC-dF$_1$Fo co-IP (FIG. 1) correlated with a significant inhibition of F$_1$Fo ATPase activity (FIG. 2).

EXAMPLE 3

δPKC Co-IPs with dF$_1$Fo Following Prolonged Hypoxia (Hx) in Neonatal Cardiac Myocytes (NCMs)

Figure 3A:
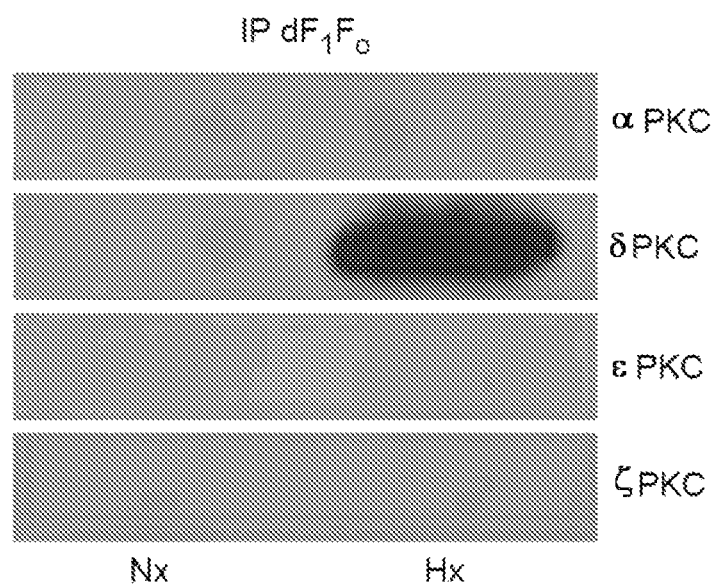
FIGS. 3A-3B: Prolonged hypoxia (Hx) induces the co-immunoprecipitation (co-IP) of δPKC with the "d" subunit of $F_1Fo$ ATP synthase ($dF_1Fo$) in neonatal rat cardiac myocytes (NCMs). NCMs were exposed to normoxia (Nx) or Hx for 4 hr in an anaerobic chamber (<0.5% oxygen). Mitochondrial isolation and co-IPs were conducted as in FIG. 1.
Figure 3B:
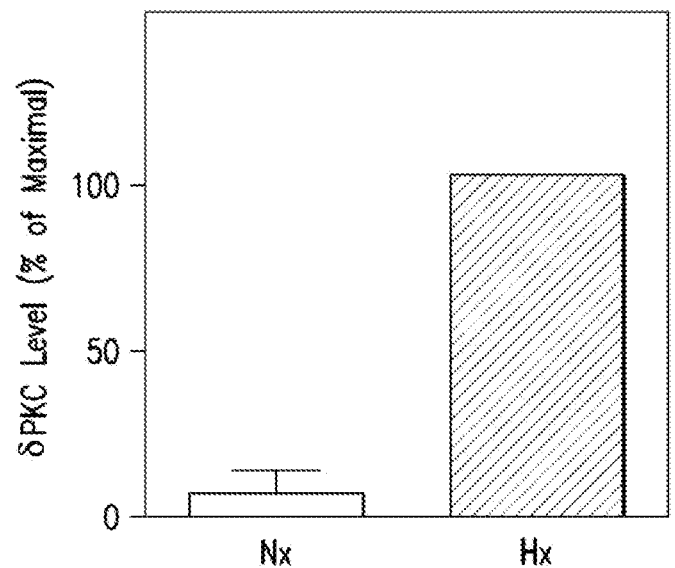

The work in FIGS. 1 and 2 involved treating NCMs with a well known PKC activator (4-β PMA) to determine its' effects on the δPKC-dF$_1$Fo Co-IP and F$_1$Fo ATPase function. It was next determined if these events could be induced in a model of cardiac ischemic injury. NCMs were therefore, exposed to 4 hr of Hx in a PlasLabs anaerobic chamber. Mitochondria were then isolated via Percoll/Optiprep gradients and subjected to dF$_1$Fo IP. As in the studies with 4-β PMA, the resulting blots showed positive immunoreactivity for only the δPKC isozyme, suggesting that prolonged Hx exposures also induce a δPKC-dF$_1$Fo co-IP (FIG. 3).

EXAMPLE 4

Exposure of NCMs to 4 hr Hyoxia (Hx) Inhibits F$_1$Fo Activity

Figure 4:
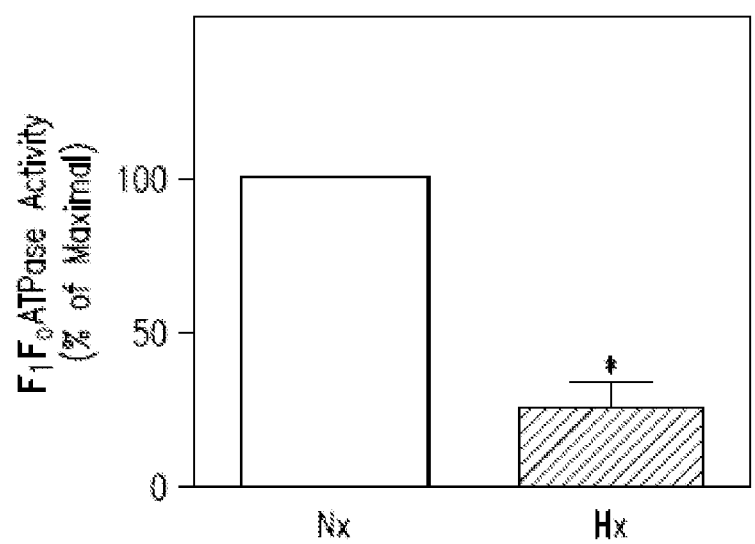
FIG. 4: Hypoxia (Hx) inhibits neonatal cardiac myocyte (NCM) $F_1Fo$ ATPase activity. NCMs were exposed to normoxia (Nx) or 4 hr. of Hx in an anaerobic chamber. Measurement of the $F_1Fo$ ATPase activity was conducted as in FIG. 2. Results are expressed as mean±S.E. from 4 independent experiments, each conducted in triplicate using samples from 4 different myocyte preparations. The asterisk indicates statistically significant differences between Nx and Hx groups ($p<0.0001$).

Whether limited Hx also inhibited F$_1$Fo ATPase activity was determined next. In FIG. 4 (F8), NCMs were exposed to 4 hr of Hx in an anaerobic chamber (77,78), which in NCMs causes minimal cell death. No significant release of rat cardiac troponin I (cTnI) into NCM media following control or 4 hr Hx treatments was observed. However, under the same conditions there was a 75.1±8,6% inhibition of baseline F$_1$Fo ATPase activity. Therefore, in addition to 4-β PMA inducing F$_1$Fo ATPase inhibition under normoxic (Nx) conditions, a 4 hr Hx exposure also decreased F$_1$Fo ATPase activity. Thus, inhibition of F$_1$Fo ATPase correlates with δPKC co-IP with dF$_1$Fo in NCMs.

EXAMPLE 5

Figure 5:
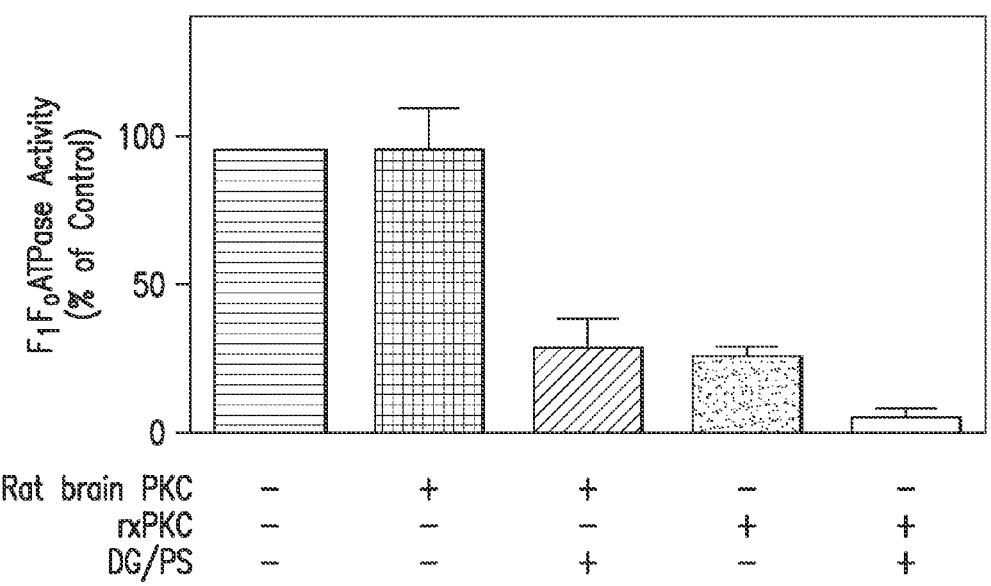
FIG. 5: Exogenously added purified rat brain PKC or recombinant δPKC, in the presence of PKC activators, inhibits in vitro $F_1Fo$ ATPase activity. Rat brain PKC (80) was added to 50 μg of rat heart $F_1Fo$ ATPase holo-enzyme purified as previously described (79). Assay length was 5 minutes in the presence of the PKC activating lipids diacylglycerol (DC)

Incubation of Purified F$_1$Fo ATPase with Activated PKC Inhibits F$_1$Fo ATPase Activity in Vitro Adult rat cardiac ventricular F$_1$Fo ATPase holo-enzyme was purified chromatographically (79) and (50 µg) was pre-incubated for 5 minutes at room temperature with diacylglycerol (DG) (0.32 mg/ml), and phosphatidylserine (PS) (24 µg/ml), and either 500 nM rat brain PKC (200 units/mg) purified as described (80), or 2 µg recombinant δPKC purified from sf9 cells. Oligomycin-sensitive F$_1$Fo ATPase activity was then monitored (FIG. 5). There was no significant F$_1$Fo ATPase activity in these PKC preparations nor was there detection of PKC activity or immunoreactivity in the F$_1$Fo ATP synthase preparations. However, F$_1$Fo ATPase activity was inhibited by 3.9±0.5-fold when purified rat brain PKC and DG/PS were included in the assay (FIG. 5, $3^{rd}$ bar from left). In addition, recombinant δPKC profoundly inhibited F$_1$Fo ATPase activity in the presence or absence of the PKC activators DG and PS (FIG. 5, 2 right-most bars).

It was investigated why F$_1$Fo ATPase activity was inhibited when recombinant δPKC was added in the absence of PKC activators? It is difficult to interpret results from in vitro PKC add-back experiments because the natural ratios of δPKC to F$_1$Fo ATP synthase are not likely to be conserved. Further, recombinant δPKC expressed in sf9 insect cells has been shown to differ in its kinetics and other features from true mammalian δPKC. Also, it is not certain that all PKC activating lipids are absent from these PKC and F$_1$Fo preparations. Finally, there have been reports of PKC isozymes modulating the activity of other enzymes by simply binding to them without phosphorylating them (81,82). Even with these limitations of the PKC add-back experiments one may still maintain that the only effect of recombinant δPKC in these assays was inhibition. This observation taken collectively with other supporting experimentation is consistent with δPKC having an inhibitory effect on the F$_1$Fo complex. These effects were lost if PKC preparations were heated at 85° C. prior to addition to the F$_1$Fo ATP synthase preparation.

EXAMPLE 6

δPKC Binds Directly to the d Subunit of F$_1$Fo Atpase (dF$_1$Fo) in Overlay Assays F$_1$Fo ATP synthase holo-enzyme was isolated (79) and individual F$_1$Fo ATP synthase subunits were resolved by SDS-PAGE, transferred to nitrocellulose paper (NCP), and subjected to the PKC overlay assay (83). When NCP containing re-solved F$_1$Fo ATP synthase subunits was "overlaid" with purified rat brain PKC (mixture of PKC isozymes) (80) in the presence of the PKC-activating lipids DG and PS, δPKC bound to a protein that co-migrated with dF$_1$Fo immunoreactivity (FIGS. 6A-6B). There also appeared to be δPKC binding to an unknown protein of 35 kDa. Interestingly, the g subunit of F$_1$Fo ATPase is approximately 35 kDa. Addition of 1 mM CaCl$_2$ to the assay appeared to reduce the DG/PS-induced δPKC binding to dF$_1$Fo, but had minimal effects on δPKC binding to the ~35 kDa protein (FIG. 6A, lane 4). The δPKC-dF$_1$Fo binding was also induced when DG/PS was replaced by 200 mM cardiolipin (CL). CL also induced δPKC binding to the ~35 kDa protein to an extent similar to that induced by DG/PS (FIG. 6A, lane 3 vs. 5). CL revealed the presence of at least 4 additional δPKC binding proteins in the purified F$_1$Fo preparations (FIG. 6A, top). This suggested that δPKC may regulate the F$_1$Fo ATPase via multiple protein-protein interactions with additional F$_1$Fo ATPase subunits or accessory proteins. These latter binding events were not observed in the absence of CL even when DG/PS were present (FIG. 6A, lanes 5-7 vs. lanes 3-4). Collectively, these results suggested a direct, PKC activator-dependent, in vitro binding interaction between δPKC and dF$_1$Fo.

Figure 7E:
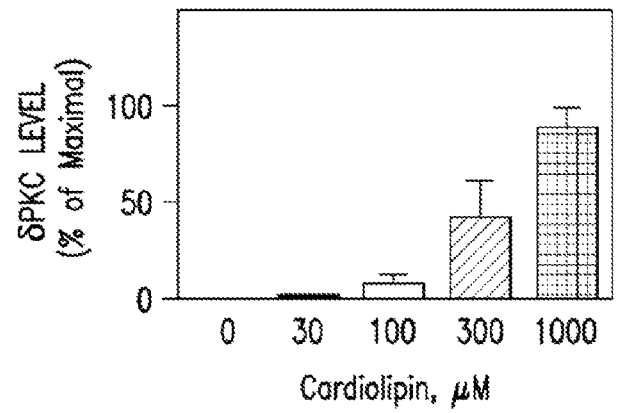

EXAMPLE 7

δPKC, but not α, ε, or ζPKC Binds to dF$_1$Fo in a Cardiolipin-Dependent Manner Gradient-purified mitochondria (100 µg) from adult rat cardiac left ventricles were subjected to SDS PAGE and electrotransfer onto nitrocellulose paper (NCP). NCP strips were incubated with purified rat brain PKC (500 nM; 200 units/mg) in the presence of DG (2 µg), PS (10 µg), and cardiolipin (0-1000 µM) as described (83,84), Lane C in FIGS. 7A-7D is an overlay strip that was not incubated with PKC or activators and instead was probed with anti-dF$_1$Fo subunit antisera to mark the position of dF$_1$Fo. All other strips were "overlayed" for 1 hr with PKC, DG and PS in the presence of 0 (lane 1), 30 (lane 2), 100 (lane 3), 300 (lane 4) or 1000 (lane 5) µM concentrations of cardiolipin. Blots were then probed for αPKC (FIG. 7A), εPKC (FIG. 7B), ζPKC (FIG. 7C) and δPKC (FIG. 7D). Only δPKC was found to have bound to dF$_1$Fo (FIG. 7E). Other proteins bound to δPKC as well which may reflect additional binding interactions between δPKC and other subunits of $F_1Fo$ ATPase or their accessory proteins which may co-purify with them.

EXAMPLE 8

2-D Separations Reveal δPKC Binding to $dF_1Fo$

Chromatographically-purified $F_1Fo$ ATPase subunits were resolved by 2-dimensional electrophoresis using a non-linear pH 3-10 IPG strip in the first dimension and SDS PAGE in the second dimension. Proteins were then electro-transferred onto NCP. FIGS. 8A-8C were probed in Western blots with antisera to the α, β, and "d" subunits of $F_1Fo$ ATPase, respectively. FIG. 8D is a 2-D blot which was incubated with purified PKC, and activators (including 30 µM cardiolipin). This blot was then probed with anti-δPKC antisera. These experiments confirmed that δPKC binds to a protein with an identical pI as $dF_1Fo$ and co-localizes with $dF_1Fo$ immunoreactivity (FIG. 8C).

EXAMPLE 9

High Glucose Induces δPKC Co-Immunoprecipitation (Co-IP) with $δF_1Fo$ which Correlates with Inhibition of $F_1Fo$ ATPase Activity in Neonatal Cardiac Myocytes NCMs were cultured in normal (5.5 mM) and high glucose (30 mM) media and were exposed to normoxia (Nx) or 4 hr of hypoxia (Hx) in an anaerobic chamber. In NCMs, 4 hr of Hx causes minimal cell death. There was no significant release of rat cardiac troponin I (cTnI) into NCM media following control or 4 hr Hx treatments. Injured cardiac myocytes release a proteolyzed fragment of cTnI (85) which can be detected in assays. cTnI release into serum is also the preferred clinical biochemical marker of myocardial infarction. In FIG. 9A, mitochondria were subjected to IP using anti-$dF_1Fo$ antisera. IPs were then subjected to Western blot analyses using antisera against PKC. δPKC. δPKC co-IPed with $dF_1Fo$ following Hx and/or high glucose exposure. This co-IP was increased when NCMs exposed to 30 mM glucose were subjected to 4 hr of Hx. Thus, hyperglycemia may induce the δPKC-$dF_1Fo$ interaction prior to Hx to diminish NCM ATP levels which makes them more sensitive to Hx injury. In FIG. 9B, $F_1Fo$ ATPase activity was measured using gradient-purified mitochondria (78,86,87). There was a 10±3-fold Hx-induced inhibition of $F_1Fo$ ATPase activity. High glucose also induced 56.1±18.1% inhibition of $F_1Fo$ ATPase activity and its combination with Hx further inhibited the activity by an additional 28±12%. These results suggest that δPKC interacts with $dF_1Fo$, to inhibit $F_1Fo$ ATPase function in hyperglycemia and hypoxia.

EXAMPLE 10

Hemodynamic Parameters of Hearts Isolated from Control and Steptozotocin (STZ)-Treated Rats The drug streptozotocin when injected into rats leads to destruction of pancreatic β-cells and greatly diminished insulin secretion, Langendorff heart preparations isolated from Sprague-Dawley rats 6 weeks after saline (con) or STZ injections were equilibrated at 37° C. for 20 minutes. Hearts were then subjected to 30 min of global ischemia followed by 90 min of reperfusion. The characteristics and hemodynamic data for each animal group are summarized. STZ-treated rats have lower body weight. Heart rate, maximal positive and negative dP/dt were lower in the STZ-treated isolated Langendorff hearts at baseline, and during reperfusion. These results show characteristic declines in the cardiac function of diabetic hearts.

Figure 10A:
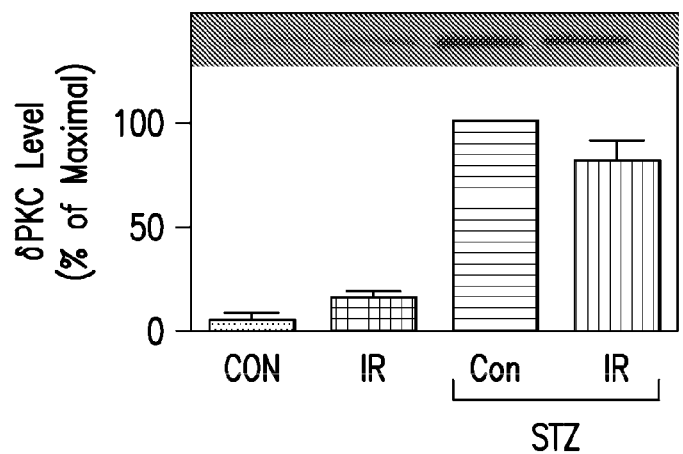
Figure 10B:
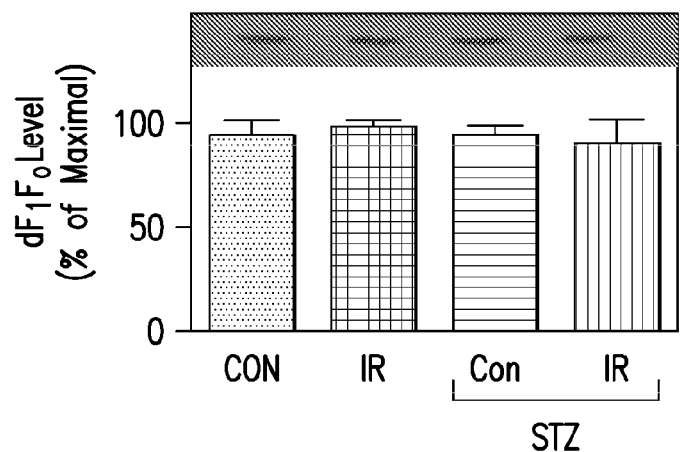
Figure 10C:
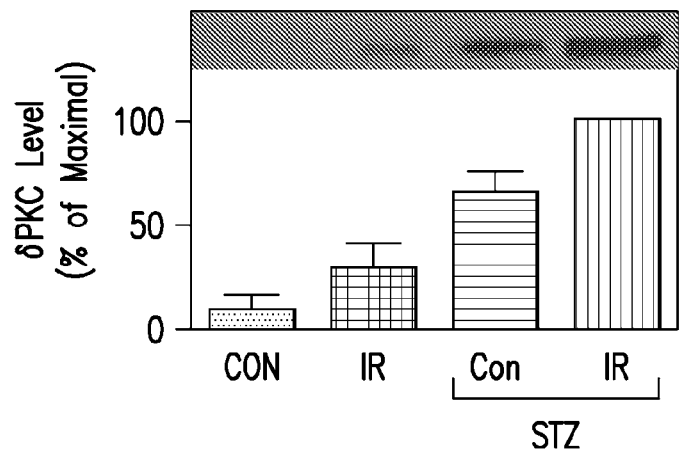
Figure 10D:
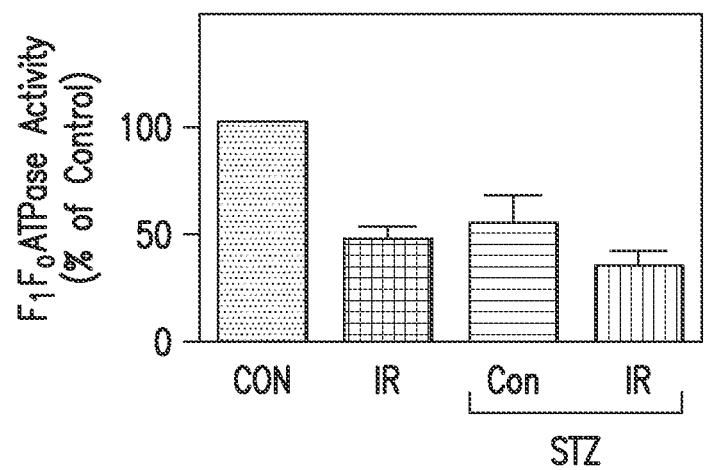
Figure 10E:
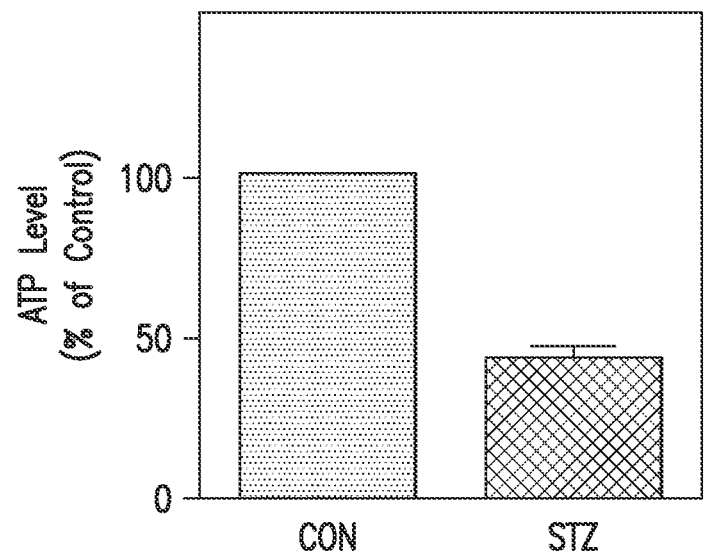

EXAMPLE 11

δPKC Co-IP with $□F_1Fo$ Correlates with Inhibition of $F_1Fo$ ATPase Activity in Diabetic Rat Hearts Langendorff heart preparations were isolated and left ventricles were harvested and mitochondria were isolated (23, 87). Mitochondria (100 µg) were subjected to Western blot analyses using antisera against δPKC (FIG. 10A) or $dF_1Fo$ (FIG. 10B). There was a modest increase in mitochondrial δPKC levels following a prolonged 20 minute ischemia/90 minute reperfusion (IR) exposure (FIG. 10A). In addition, in hearts isolated from rats, 6 weeks after STZ injection, there was a greater than 10-fold increase in mitochondrial δPKC levels, which was not further increased when these hearts were exposed to IR (FIG. 10A). In contrast, none of these treatments altered the mitochondrial levels of the $dF_1Fo$ protein in Western blots (FIG. 10B). In FIG. 10C, mtochondria, isolated from hearts of non-STZ- or STZ-treated rats, were subjected to IP protocols. In control rats, an IR exposure induced a significant co-IP of δPKC with $dF_1Fo$ antisera. The δPKC-$δF_1Fo$ co-IP was also strongly induced by STZ alone, and only modestly increased when STZ hearts were exposed to IR (FIG. 10C). In FIG. 10D, $F_1Fo$ ATPase activity was measured in mitochondria from each treatment group shown in FIG. 10C. IR alone caused a 2.2±0.3-fold inhibition of activity. STZ alone produced a very similar inhibitory effect on $F_1Fo$ ATPase, the magnitude of which was not significantly increased when STZ rat hearts were exposed to prolonged IR. Finally, in FIG. 10E, it was demonstrated that STZ exposure decreased myocardial ATP levels by 2.3±0.1-fold. Collectively, these results support the hypothesis that STZ treatment of rats promotes the δPKC-$dF_1Fo$ co-IP which correlates with an inhibition of $F_1Fo$ ATPase activity. It further suggests that STZ treatment maximally induces this δPKC-$dF_1Fo$ interaction and subsequent exposure of hearts to IR injury does not significantly increase the δPKC-$dF_1Fo$ co-IP or inhibition of $F_1Fo$ ATPase activity. This hyperglycemia-induced decrease in $F_1Fo$ ATPase activity may make diabetic hearts more sensitive to IR injury via a chronic reduction in ATP synthase capacity.

EXAMPLE 12

Development of $dF_1Fo$-Derived Peptides to Modulate the δPKC-$dF_1Fo$ Interaction Since the δPKC-$dF_1Fo$ interaction correlated with inhibition of $F_1Fo$ activity following phorbol ester, Hx, and hyperglycemia, peptides were developed to modulate the δPKC-$dF_1Fo$ interaction in vivo. Fourteen different peptides were characterized for their ability to modulate the binding of $dF_1Fo$ to δPKC in overlay assays. The amino acid structures of the 14 original peptides are shown in FIG. 11. The peptides in FIG. 11 are sequential amino acid sequences beginning at the N-terminus of $dF_1Fo$ and preceding to the C-terminus. Each peptide has a 5 amino acid overlap with the previous sequential peptide.

EXAMPLE 13

PKC Overlay Assays Reveal an Inhibitor (Antagonist) and a Facilitator (Agonist) of the δPKC-dF$_1$Fo Binding Interaction As shown in FIG. 11, a series of sequential dF$_1$Fo peptides (one 15-mer, 13 different 16 amino acid peptides and one 18-mer) were synthesized that cover the entire sequence of dF$_1$Fo. One peptide AGRKLALKTIDWVSF (SEQ ID NO: 1; FIG. 11) demonstrated a dose-dependent inhibition of the δPKC-dF$_1$Fo binding interaction (FIG. 12A), while another peptide RVREYEKQLEKIKNMI (SEQ ID NO: 2; FIG. 11) facilitates the binding of δPKC to dF$_1$Fo (FIG. 12B) with each peptide having an IC$_{50}$ of about 0.3 mM. At the top of each histogram in FIGS. 12A-12B are representative autoradiographs demonstrating in vitro δPKC binding to purified dF$_1$Fo. Histograms document mean±S.E. values from a minimum of 5 independent experiments. Two different lots of peptides and 3 separate preparations each for F$_1$Fo ATP synthase subunits and purified PKC were used.

EXAMPLE 14

Cell-Permeable, Mitochondrial-Targeted Versions of the δPKC-dF$_1$Fo Modulating Peptides Peptides do not readily traverse biological membranes and in most cases, are cell impermeable. Therefore, to evaluate the effects of disrupting (antagonist/inhibitor) or facilitating (agonist/facilitator) the δPKC-dF$_1$Fo interaction, in intact cardiac cells and tissues, the human immunodeficiency virus (HIV) Tat protein transduction domain (PTD; SEQ ID NO: 18) (88) was added to the N-terminal of the dF$_1$Fo-derived peptides. The HIV Tat PTD is attached as described (89) via a cysteine-cysteine linkage, which is thought to be cleaved off after cellular uptake of the peptide. Therefore, to improve mitochondrial uptake once the dF$_1$Fo-derived peptides were inside cells, a mitochondrial targeting sequence (SEQ ID NO: 19) from the number IV subunit of cytochrome oxidase (90) was also added. Next, a Flag epitope tagging sequence (SEQ ID NO: 20) was included at the C-terminus of the peptides to monitor mitochondrial uptake. All amino acid sequences are indicated above by single letter amino acid code inside the box depicting each of these domains (FIG. 13). The top peptide describes the δPKC-dF$_1$Fo inhibitor sequence, and the bottom peptide contains the δPKC-dF$_1$Fo facilitator peptide. These are also the planned form of the peptides for use in human therapeutics. However, since the Flag epitope does not contribute to the ability of the peptides to modulate δPKC-dF$_1$Fo interaction, nor does it play a role in the targeting of the peptides, it is likely that the peptides in human therapeutics will not include the Flag epitope. One exception to this could be if one needs to monitor stability of the peptides or test their tissue and cell organelle localization in biopsies or in post-mortem procedures. It is also possible the Flag sequence may itself convey resistance of these peptides to proteolysis.

EXAMPLE 15

An HIV Tat-Coupled, Mitochondrial-Targeted Version of the δPKC-dF$_1$Fo Inhibitor is Delivered to Percoll/OptiPrep-Purified Cardiac Mitochondria A cell permeable, mitochondrial-targeted version of the δPKC-☐F$_1$Fo inhibitor YGRKKRRQRRR-MLATRALS-LIGKRAISTSVC-AGRKLALKTIDWVSF-DYKDDD DK (SEQ ID NO: 3) and facilitator YGRKKRRQRRR-MLA-TRALSLIGKRAISTSVC-RVRE YEKQLEKIKNMI-DYKDDDDK (SEQ ID NO: 4) peptides was developed. The extensive sensitivity of the dF$_1$Fo antagonist peptide alone (no cells present) to digestion with 100 units 1 ml of trypsin for 20 minutes (FIG. 14, lanes 1 vs. 2) was demonstrated. Next, NCMs were incubated in the absence of peptide (FIG. 14, lanes 3-4) or in the presence of 100 nM concentrations of the HIV-Tat coupled, mitochondrial-targeted antagonist peptide for 2 hrs at 37° C. (FIG. 14, lanes 5-6). Mitochondria were then isolated and subjected to Western blot analysis using anti-Flag antisera. As predicted NCMs not incubated with the Tat-coupled, mitochondrial-targeted antagonist showed no Flag immunoreactivity (FIG. 14, lanes 3-4). However, there was substantial uptake of the peptide into gradient-purified mitochondria indicating that the peptide entered NCMs and was targeted to mitochondria (FIG. 14, lane 5). This peptide uptake was not altered when mitochondria, isolated from NCMs that had been preincubated with peptide, were incubated with 100 units/ml of trypsin (FIG. 14, lane 6). This confirmed that the Flag-tagged peptide was not simply adhering to extra-mitochondrial surfaces.

EXAMPLE 16

Hypoxia- and Hyperglycemia-Induced Inhibition of F$_1$Fo ATPase Activity is Attenuated by the Cell-Permeable δPKC-dF$_1$Fo Antagonist in NCMs Cells were cultured in normal or high glucose for 24 hrs as described above. Next, each treatment group was preincubated with a scrambled sequence (control) peptide or 10 nM δPKC-dF$_1$Fo inhibitor peptide for 2 hr., followed by 4 hrs of either Nx, or Hx in an anaerobic chamber. Mitochondria were isolated and assayed for F$_1$Fo ATPase activity. Hx alone inhibited the basal oligomycin-sensitive F$_1$Fo ATPase activity by 79+2.4%. This inhibition of activity was reversed by 51±5.3% in NCMs preincubated with the δPKC-dF$_1$Fo inhibitor peptide. High glucose induced 54±13% inhibition of F$_1$Fo ATPase activity and its combination with Hx further inhibited the activity by an additional 29±8%. The mitochondrially-targeted δPKC-dF$_1$Fo inhibitor in high glucose plus Hx groups attenuated the inhibition of activity by 34+2%. These results demonstrated that the δPKC-dF$_1$Fo co-IP correlated with a significant inhibition of F$_1$Fo ATPase activity, suggesting potential regulation of the F$_1$Fo complex under high glucose conditions, and this inhibition can be attenuated by preincubation with the δPKC-dF$_1$Fo inhibitor peptide.

EXAMPLE 17

Cardiac Subsarcolemmal and Interfibrillar Mitochondria

The heart has two major populations of mitochondria termed subsarcolemmal (SSM) and interfibrillar (IFM) mitochondria (91). SSM exist just below the plasma membrane or sarcolemma and are thought to play important roles in providing energy for key sarcolemmal enzymes such as the sodium potassium ATPase and other ATP-consuming enzymes in the vicinity of the plasma membrane. IFM are positioned more deep inside of cardiac myocytes between the myofibrils and likely provide energy for contraction, SERCA pumps and other processes. There are many more IFM than SSM in the mammalian heart, yet most studies of cardiac injury concentrate on SSM due to their ease of isolation.

EXAMPLE 18

Cell-Permeable Mitochondrial-Targeted δPKC-dF$_1$Fo Inhibitor Enters SSM and IFM Mitochondria Following Delivery to Isolated Rat Hearts Following equilibration, Langendorff heart preparations were retrograde-perfused with 20 nM concentrations of the δPKC-dF$_1$Fo antagonist for 20 (FIG. 15A) or 60 (FIG. 15B) minutes. The left (L) and right (R) ventricles were then removed and SSM and IFM were isolated as described by Hoppel (91). All mitochondria were further purified using Percoll/Optiprep gradients (23,78,86,87). Western blot analyses for Flag immunoreactivity were then conducted. Whether the right ventricular SSM and IFM could serve as an indirect indicator of peptide uptake in the left ventricular mitochondria was determined. In FIG. 15, "L" refers to left ventricle and "R" stands for right ventricle. The results indicate that one can estimate left ventricular peptide uptake in the SSM, but it is more difficult to estimate IFM levels in left ventricle using right ventricular samples (FIGS. 15A-15B). Possibly the use of additional right ventricular tissue combined with chromatography or other enrichment techniques may also allow one to estimate IFM uptake of peptides using this approach. Nonetheless, it is clear that delivery of the peptide to SSM was more efficient than delivery to IFM. However, substantial delivery to IFM was observed following a 60 minute perfusion. In addition, the peptides of the present invention may inhibit or enhance F$_1$Fo ATP synthase activity at concentrations below the level of Flag immuno-detection. The "antagonist" peptide was delivered to both SSM and IFM using the Langendorff method. When mitochondria isolated from hearts perfused with the Flag epitope-tagged inhibitor peptide were incubated in vitro with trypsin (FIGS. 15A-15B) there was no loss in Flag immunoreactivity. Thus, the antagonist peptide was inside the SSM and IFM and not attached to extra-mitochondrial surfaces.

EXAMPLE 19

The Inhibitor of the δPKC-dF$_1$Fo Interaction Reduces Infarct Size, and the δPKC-dF$_1$Fo Facilitator Peptide Increases Infarct Size, Induced by Prolonged Ischemia/Reperfusion (IR) Exposure in Isolated Rat Hearts The effects of the peptides of the present invention on infarct size following IR injury in the Langendorff model was assessed, Hearts were perfused in the absence of peptide, under normoxic conditions for 110 minutes (Con), or were given a 20 minute global, no flow, ischemia exposure followed by normoxic perfusion for 90 minutes. δPKC-dF$_1$Fo modulatory peptides (20 nM) were administered at the onset of reperfusion for 20 minutes. (FIG. 16, bottom 3 panels). The IR group (FIG. 16, second panel from top) received a scrambled sequence (inactive) peptide ADKIGWAVLRTK-SLF (SEQ ID NO: 5) derived from the sequence of the antagonist peptide (Complete amino acid sequence shown in FIG. 13). The "antagonist" group was administered the δPKC-dF$_1$Fo inhibitor (FIG. 16, third panel from top) and the "agonist" group received the δPKC-dF$_1$Fo facilitator peptide (FIG. 16, bottom panel). All peptides contained the HIV-Tat, mitochondrial targeting, and Rag epitope sequences and all target to the mitochondria. Following IR exposures hearts were rinsed in Kreb's buffer and left ventricles were subjected to sectioning and infarct staining using standard triphenyltetrazolium chloride (TTC) techniques. Following a 20 min ischemia and 90 min reperfusion, infarction (white color) was observed in ~40% of the left ventricle area (IR).

In hearts receiving the δPKC-dF$_1$Fo antagonist, infarct size was reduced by 34±8% (n=5) (FIG. 17). Similarly, the δPKC-dF$_1$Fo antagonist reduced rat cardiac troponin I fragment release from these hearts by 55±11% (n=5) compared to the inactive scrambled sequence peptide (FIG. 18). In FIG. 18 Langendorff hearts were perfused with no peptide (IR) or the scrambled sequence or δPKC-dF$_1$Fo inhibitor peptides during the first 20 minutes of reperfusion as in FIGS. 16-17. In contrast, in hearts perfused with the PKC-dF$_1$Fo agonist peptide, infarction was enhanced by 27±3% (n=3). TTC and cTnI measurements were performed immediately following the 20 minute ischemia/90 minute reperfusion insult. It is likely that such measurements made a few days after the IR insult in animals would demonstrate even greater protection because cardiac cell death continues well after the heart attack. δPKC inhibits F$_1$Fo ATP synthase during IR injury and the δPKC-dF$_1$Fo antagonist reduces infarction by inhibiting the δPKC-dF$_1$Fo interaction and relieving the inhibitory effect on the F$_1$Fo ATP synthase. When administered at the time of oxygenated reperfusion the δPKC-dF$_1$Fo agonist peptide enhances the inhibition of F$_1$Fo ATP synthase by δPKC during IR injury which increases infarct size. It is possible, however that if the δPKC-dF$_1$Fo facilitator is given prior to ischemia or in a more chronic condition such as diabetes or cancer it could have beneficial effects.

The present invention describes 2 novel, cell-permeable, mitochondrially-targeted peptides. These peptides modulate the activity of the F$_1$Fo ATP synthase, the enzyme responsible for over 90% of cardiac ATP production. These dF$_1$Fo-derived peptides may be synthesized chemically to contain well-characterized protein transduction amino acid sequences (88) to allow them to be readily taken up by cells. In addition, since these peptides modulate the F$_1$Fo ATP synthase, which exists in the inner mitochondrial membrane, a mitochondrial-targeting motif derived from the number IV subunit of cytochrome oxidase (90) may be included. Finally, a Flag epitope tagging sequence can be incorporated into the peptides to monitor their uptake into mitochondria. The Flag sequence is not necessary for their biochemical actions and is used only to demonstrate mitochondrial targeting and stability of the peptides in cardiac mitochondria and tissue or in serum. However, the Flag epitope could affect the lability of the peptides to proteolysis in vivo.

In laboratory models one of the peptides protects (inhibitor) heart cells against injury by IR (simulated heart attack) or hyperglycemia (diabetes) insults, whereas the other peptide (facilitator) exacerbates damage when the peptides are administered at the time of reperfusion after prolonged ischemia. Mechanistically; the cardioprotective peptide interferes with the inhibition of F$_1$Fo activity by a second enzyme known as delta protein kinase C (δPKC). The second dF$_1$Fo-derived (injury-exacerbating) peptide has the opposite action to enhance the δPKC-mediated inhibition of F$_1$Fo activity. An inhibitory effect on the F$_1$Fo ATP synthase is highly significant in the context of ischemic or diabetic heart disease because it could amplify damage by substantially decreasing cardiac ATP (energy) levels.

In contrast, during myocardial ischemia the F$_1$Fo complex can operate in reverse as an ATPase and is a primary mechanism by which ATP is lost during a heart attack. In that context the peptide which enhances δPKC-mediated inhibition of F$_1$Fo ATPase activity could also be beneficial. It may depend entirely on when each peptide is given (e.g. before or after a cardiac ischemic insult) as to whether protection or exacerbation of damage occurs. The present invention indicates that when the δPKC-dF$_1$Fo antagonist is administered at reperfusion it is protective. In contrast, the δPKC-dF$_1$Fo facilitator peptide exacerbates IR when given at the time of cardiac reperfusion. Therefore, the δPKC-dF$_1$Fo antagonist peptide can be used as a cardioprotective pharmaceutical.

It is possible that experimentation with amino acid sequences found in the dF$_1$Fo protein may ultimately identify smaller peptidomimetic drugs or additional peptide sequences with therapeutic value. The δPKC-dF$_1$Fo antagonist peptide reduces cardiac death caused by IR injury (simulated heart attacks) or hyperglycemia. Studies suggest that it accomplishes this by blocking the binding of δPKC to dF$_1$Fo, which in-turn relieves a potent inhibitory effect on F$_1$Fo ATP synthase. Enhanced recovery of ATP levels following a heart attack or in other diseases benefits and preserves hundreds of enzymatic processes resulting in reduced myocardial infarct size and improved recovery of cardiac function. Similarly, many studies have indicated decreased energy production may play an important role in the cardiac pathologies associated with diabetes. Chronic induction of the δPKC-dF$_1$Fo interaction during hyperglycemia may also contribute to exacerbation of IR injury following a heart attack in diabetics. Further, it is well known that cancer cells typically become less dependent of OXPHOS for energy production. Further, a recent report (Cancer Res. (2005) 65 (8):3162-70) indicates anti-tumorigenic actions when siRNA is used to inhibit expression of the d subunit of F$_1$Fo ATP synthase. δPKC clearly plays significant roles in cancer and it is currently unknown if the δPKC-dF$_1$Fo interaction plays a role in this shift in metabolism. Therefore, these peptides may have utility in cancer therapy. There are currently no cardio-protective or other therapeutics which directly modify F$_1$Fo ATP synthase or ATPase function.

The following references may have been cited herein:
1. Bashore, et al., (2008) Heart Disease, in Current Medical Diagnosis and Treatment, Tierney, L. M. Ed., McGraw Hill Medical, New York, pp. 280-369.
2. Garcia, et al., *Diabetes*. 23:105-111, 1974.
3. Hartwell, et al., (2005) *Health Technol. Assess*. 9:1-99.
4. Murphy, E. and Steenbergen, C. (2008) *Physiol. Rev*. 88:581-609.
5. Nishizuka, Y. (1988) *Nature* 334:661-665.
6. Quest, A. F. G. and Bell, R. M. (1994) In *Protein kinase C* (Kuo, J. F., Ed) pp. 64-95, Oxford Univ. Press, New York.
7. Mackay, K. and Mochly-Rosen, D. (2001) *J. Mol. Cell. Cardiol*. 33:1301-1307.
8. Kheifets V. and Mochly-Rosen, D. (2007) *Pharmacological Res*. 55:467-476.
9. Disatnik, et al., (1995) *J. Mol. Cell. Cardiol*. 27:2473-2481.
10. Battaini, F. and Mochly-Rosen, D. (2007) *Pharmacological Res*. 55:461-466.
11. Nguyen, at al., (2007) *Curr. Enz. Inhib*. 3:143-159.
12. Murriel, at al., (2004) *J. Biol. Chem*. 279: 47985-47991.
13. Inagaki, at al., (2003) *Circulation* 108:2304-2307.
14. Churchill, et al., (2005) *Circ. Res*. 97:78-85.
15. Churchill, et al., (2005) *Arch. Biochem. Biophys*. 439: 194-199.
16. Inagaki, et al., (2006) *Cardiovasc. Res*. 70:222-230.
17. Murry, at al., (1986) *Circulation* 74:1124-1136.
18. Liang B. T. (1997) *Am. J. Physiol. Heart Circ. Physiol*. 273:H847-H853.
19. Baines, et al., (2003) *Circ. Res*. 92:873-880.
20. Bertolotto, et al., (2000) *J. Biol. Chem*. 275: 37246-37250.
21. Baines, at al., (2002) *Circ. Res*. 90:390-397.
22. Gubina, et al., (1998). *Blood*. 91:823-829.
23. Guo, et al., (2007) *Am. J. Physiol, Heart Circ. Physiol*. 293:H2219-H2230,
24. Mayr, et al., (2004) *Am. J. Physiol. Heart Circ. Physiol*. 287:H937-H945.
25. Mayr, et al., (2004) *Am. J, Physiol. Heart Circ. Physiol*. 287:H946-H956.
26. DELTA MI Investigators (2008) *Circulation* 117:886-896.
27. Inoguchi et al., (1992) *Proc. Natl. Acad. Sci. USA*. 89:11059-11063.
28. Xiang, et al., (1992) *Biochem. Biophys. Res. Commun*. 187:703-710.
29. Bilim, et al., (2008) *Cardiovasc. Diabetol*. 7:2.
30. Arikawa, et al., (2007) *Diabetes*. 56:1410-1420.
31. Xia, et al., (2007) *Cardiovasc. Res*. 73:770-782.
32. Giles, et al., (2002) *Alcohol Clin. Exp. Res*. 26:1123-1133.
33. Malhotra, et al., (2001) *Diabetes* 50:1918-1926.
34. Schaffer, et al., (1997) *Cardiovasc. Res*. 34:129-136.
35. Wickley, et al., (2006) *Anesthesiology* 104:978-987.
36. Reuter, et al., (2008) *Mol. Cell. Biochem*. 308:141-149.
37. Yaras, et al., (2007) *Am. J. Physiol. Heart Circ. Physiol*. 292:H912-H920.
38. Yaras et al., (2005) *Diabetes* 54:3082-3088.
39. Schaffer, et al., (1997) *Cardiovasc. Res*. 34:129-136.
40. Lin, et al., (2006) *Mol. Cell Biochem*. 290:69-78.
41. Lin, et al., (2008) *J Physiol Pharmacol*. 59:271-285.
42. Farese, et al., (2007) *J. Clin. Invest*. 117:2289-2301.
43. Xia, et al., (2007) *Cardiovasc. Res*. 73:770-782.
44. Wakasaki, et al., (1997) *Proc. Natl. Acad. Sci. USA*. 94:9320-9325.
45. Malhotra, et al., (2005) *Am. J. Physiol. Heart Circ. Physiol*. 289:H1343-H1350.
46. Arikawa, et al., (2007) *Diabetes*. 56:1410-1420.
47. Boudina, et al., (2007) *Circulation* 115:3213-3223.
48. Hutteman, et al., (2008) *J. Bioenerg. Biomembr*. 40:445-456.
49. Boudina, S., Abel, E. D. (2006) *Physiology (Bethesda)* 21:250-258.
50. An, et al., (2006) *Am. J. Physiol. Heart Circ. Physiol*. 291:H1489-H1506.
51. Seager, et al., (1984) *Br. J. Exp. Pathol*. 65: 613-623.
52. Boudina, et al., (2005) *Circulation* 112:2686-2695.
53. Kuo, et al., (1983) *Diabetes* 32:781-787.
54. Pierce. G. N., Dhalla, N. S. (1985) *Can. J. Cardiol,* 1:48-54.
55. Tanaka, et al., (1992) *Cardiovasc. Res*. 26:409-414.
56. Savabi, F. (1988) *Biochem. Biophys. Res. Comm*. 154: 469-475.
57. Awaji, et al., (1990) *Cardiovasc. Res*. 24:547-554.
58. Neely, et al., (1972) *Prog. Cardiovasc. Dis*. 15:289-329.
59. Carbajo, et al., (2005) *J. Mol. Biol*. 351:824-838.
60. Walker, et al., (2006) *Biochim. Biophys. Acta* 1757:286-296.
61. Gaballo, et al., *Curr. Protein Pept. Sci*. 3:451-460, 2006
62. Di Pancrazio, at al., (2004) *Biochim. Biophys. Acta. Bioenerg*. 1659:52-62.
63. Harris. D. A., and Das, A. M. (1991) *Biochem. J*. 280: 561-573.
64. Jennings, et al., (1991) *J. Mol. Cell. Cardiol*. 23: 1383-1395.
65. Solaini, et al., (2005) *Biochem. J*. 390:377-394.
66. Green, et al., (2000) *Biochim. Biophys. Acta* 1458:343-355.
67. Zanotti, et al., (2004) *J. Bioenerg. Biomembr*. 36, 447-457.
68. Das, A. M. (2004) *Mol. Genet. Metab*. 79, 71-82.

69. Ylitalo, at al., (2001) *Biochim. Biophys. Acta* 1504:329-339.
70. McLeod, et al. (2005) *J. Biol. Chem.* 280:33470-33476.
71. Echtay, et al., (2002) *Nature.* 415(6867):96-99.
72. Skulachev. V. P. (1999) *J. Bioenerg. Biomembr.* 31:431-445.
73. Boudina, et al., (2007) *Diabetes* 56:2457-2466.
74. Churchill, et al., (2007) *Biochem. Soc. Trans.* 35(Pt5):1040-1042.
75. Murriel, C. L., Mochly-Rosen, D. (2003) *Arch. Biochem. Biophys.* 420, 246-254.
76. Inagaki, at al., (2003) *Circulation* 108, 869-875.
77. Gray, et al., (1997) *J. Biol. Chem.* 272:30945-30951.
78. Ogbi, M. and Johnson, J. A. (2006) *Biochem. J.* 393:191-199.
79. Buchanan. S. K. and Walker, J. E. (1996). *Biochem. J.* 318:343-349.
80. Mochly-Rosen, D. and Koshland, D. E. (1987) *J. Biol. Chem.* 262:2291-2297.
81. Conricode, at al., (1992) *J. Biol. Chem.* 267:7199-7202.
82. Nishikawa, at al., (1998) *J. Biol. Chem.* 273:23126-23133.
83. Schechtman, at al., (2003) *Meth. Mol. Biol.* 233:345-350.
84. Nguyen, at al., (2008) *J. Biol. Chem.* 283:29831-29840.
85. Collinson, P. O. and Gaze, D. C. (2007) *Heart Lung Circ.* 16 Suppl 3:S71-S82.
86. Ogbi, at al., (2004) *Biochem. J.* 382:923-932.
87. Yu, at al., (2008) *Am. J. Physiol. Heart Circ. Physiol.* 294:H2037-H2045.
88. Schwarze, et al., (1999) *Science* 285:1569-1572.
89. Chen, et al., (2001) *Proc. Natl. Acad. Sci. U.S.A.* 98:11114-11119.
90. Brix, et al., (1991) *J. Biol. Chem.* 274:16522-16530.
91. Palmer, J., Tandler, B., Hoppel, C. (1977) *J. Biol. Chem.* 252:8731-8739.

Any patents or publications mentioned in this specification are indicative of the levels of those skilled in the art to which the invention pertains. These patents and publications are incorporated by reference herein to the same extent as if each individual publication was incorporated by reference specifically and individually. One skilled in the art will appreciate that the present invention is well adapted to carry out the objects and obtain the ends and advantages mentioned, as well as those of objects, ends and advantages inherent herein. Changes therein and other uses which are encompassed within the spirit of the invention as defined by the scope of the claims will occur to those skilled in the art.

What is claimed is:

1. A fusion protein consisting of, from N-terminal to C terminal, a protein transduction domain fused to a mitochondrial targeting domain fused to an isolated peptide fragment of the "d" subunit of the mammalian mitochondrial enzyme $F_1F_0$ ATP synthase consisting of an amino acid sequence at least 90% identical to the amino acid sequence of SEQ ID NO: 1, wherein the protein transduction domain consists of the human immunodeficiency virus (HIV) Tat protein transduction domain (SEQ ID NO: 18), and wherein the mitochondrial targeting domain consist of number IV subunit of cytochrome oxidase (SEQ ID NO: 19).

2. A pharmaceutical composition comprising the fusion protein of claim 1.

3. The pharmaceutical composition of claim 2, further comprising a hemostatic compound, an antimicrobial compound, an antibacterial compound, or any combination thereof.

4. A kit comprising the fusion protein of claim 1.

* * * * *

SEQUENCE LISTING

```
<160> NUMBER OF SEQ ID NOS: 20

<210> SEQ ID NO 1
<211> LENGTH: 15
<212> TYPE: PRT
<213> ORGANISM: artificial sequence
<220> FEATURE:
<223> OTHER INFORMATION: sequence of a dF1Fo peptide that dose-
      dependently inhibits dPKC-dF1Fo interaction

<400> SEQUENCE: 1

Ala Gly Arg Lys Leu Ala Leu Lys Thr Ile Asp Trp Val Ser Phe
1               5                   10                  15

<210> SEQ ID NO 2
<211> LENGTH: 16
<212> TYPE: PRT
<213> ORGANISM: artificial sequence
<220> FEATURE:
<223> OTHER INFORMATION: sequence of a dF1Fo peptide that facilitates
      dPKC-dF1Fo interaction

<400> SEQUENCE: 2

Arg Val Arg Glu Tyr Glu Lys Gln Leu Glu Lys Ile Lys Asn Met Ile
1               5                   10                  15

<210> SEQ ID NO 3
<211> LENGTH: 54
<212> TYPE: PRT
<213> ORGANISM: artificial sequence
<220> FEATURE:
<223> OTHER INFORMATION: sequence of mitochondrial-targeted inhibitor
      of dPKC-dF1Fo interaction

<400> SEQUENCE: 3

Tyr Gly Arg Lys Lys Arg Arg Gln Arg Arg Met Leu Ala Thr Arg
1               5                   10                  15

Ala Leu Ser Leu Ile Gly Lys Arg Ala Ile Ser Thr Ser Val Cys Ala
            20                  25                  30
```

```
Gly Arg Lys Leu Ala Leu Lys Thr Ile Asp Trp Val Ser Phe Asp Tyr
        35                  40                  45

Lys Asp Asp Asp Asp Lys
    50
```

<210> SEQ ID NO 4
<211> LENGTH: 55
<212> TYPE: PRT
<213> ORGANISM: artificial sequence
<220> FEATURE:
<223> OTHER INFORMATION: sequence of mitochondrial-targeted facilitator
      of dPKC-dF1Fo interaction

<400> SEQUENCE: 4

```
Tyr Gly Arg Lys Lys Arg Arg Gln Arg Arg Met Leu Ala Thr Arg
1               5                   10                  15

Ala Leu Ser Leu Ile Gly Lys Arg Ala Ile Ser Thr Ser Val Cys Arg
            20                  25                  30

Val Arg Glu Tyr Glu Lys Gln Leu Glu Lys Ile Lys Asn Met Ile Asp
        35                  40                  45

Tyr Lys Asp Asp Asp Asp Lys
    50                  55
```

<210> SEQ ID NO 5
<211> LENGTH: 15
<212> TYPE: PRT
<213> ORGANISM: artificial sequence
<220> FEATURE:
<223> OTHER INFORMATION: sequence of an inactive peptide

<400> SEQUENCE: 5

```
Ala Asp Lys Ile Gly Trp Ala Val Leu Arg Thr Lys Ser Leu Phe
1               5                   10                  15
```

<210> SEQ ID NO 6
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 6

```
Asp Trp Val Ser Phe Val Glu Ile Met Pro Gln Asn Gln Lys Ala Ile
1               5                   10                  15
```

<210> SEQ ID NO 7
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 7

```
Asn Gln Lys Ala Ile Gly Asn Ala Leu Lys Ser Trp Asn Glu Thr Phe
1               5                   10                  15
```

<210> SEQ ID NO 8
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 8

```
Trp Asn Glu Thr Phe His Thr Arg Leu Ala Ser Leu Ser Glu Lys Pro
1               5                   10                  15
```

-continued

<210> SEQ ID NO 9
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 9

Leu Ser Glu Lys Pro Pro Ala Ile Asp Trp Ala Tyr Tyr Arg Ala Asn
1               5                   10                  15

<210> SEQ ID NO 10
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 10

Tyr Tyr Arg Ala Asn Val Asp Lys Pro Gly Leu Val Asp Asp Phe Lys
1               5                   10                  15

<210> SEQ ID NO 11
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 11

Val Asp Asp Phe Lys Asn Lys Tyr Asn Ala Leu Lys Ile Pro Val Pro
1               5                   10                  15

<210> SEQ ID NO 12
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 12

Lys Ile Pro Val Pro Glu Asp Lys Tyr Thr Ala Leu Val Asp Ala Glu
1               5                   10                  15

<210> SEQ ID NO 13
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 13

Leu Val Asp Ala Glu Glu Lys Glu Asp Val Lys Asn Cys Ala Gln Phe
1               5                   10                  15

<210> SEQ ID NO 14
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 14

Asn Cys Ala Gln Phe Val Thr Gly Ser Gln Ala Arg Val Arg Glu Tyr
1               5                   10                  15

```
<210> SEQ ID NO 15
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 15

Ile Lys Asn Met Ile Pro Phe Asp Gln Met Thr Ile Asp Asp Leu Asn
1               5                   10                  15

<210> SEQ ID NO 16
<211> LENGTH: 16
<212> TYPE: PRT
<213> ORGANISM: artificial sequence
<220> FEATURE:
<223> OTHER INFORMATION: sequence of a dF1Fo peptide

<400> SEQUENCE: 16

Ile Asp Asp Leu Asn Glu Val Phe Pro Glu Thr Lys Leu Asp Lys Arg
1               5                   10                  15

<210> SEQ ID NO 17
<211> LENGTH: 18
<212> TYPE: PRT
<213> ORGANISM: artificial sequence
<220> FEATURE:
<223> OTHER INFORMATION: sequence of a dF1Fo peptide

<400> SEQUENCE: 17

Lys Leu Asp Lys Arg Lys Tyr Pro Tyr Trp Pro His Gln Pro Ile Glu
1               5                   10                  15

Asn Leu

<210> SEQ ID NO 18
<211> LENGTH: 11
<212> TYPE: PRT
<213> ORGANISM: artificial sequence
<220> FEATURE:
<223> OTHER INFORMATION: sequence of human immunodeficiency virus Tat
      protein transduction domain

<400> SEQUENCE: 18

Tyr Gly Arg Lys Lys Arg Arg Gln Arg Arg Arg
1               5                   10

<210> SEQ ID NO 19
<211> LENGTH: 20
<212> TYPE: PRT
<213> ORGANISM: artificial sequence
<220> FEATURE:
<223> OTHER INFORMATION: sequence of a mitochondrial targeting peptide

<400> SEQUENCE: 19

Met Leu Ala Thr Arg Ala Leu Ser Leu Ile Gly Lys Arg Ala Ile Ser
1               5                   10                  15

Thr Ser Val Cys
            20

<210> SEQ ID NO 20
<211> LENGTH: 8
<212> TYPE: PRT
<213> ORGANISM: artificial sequence
<220> FEATURE:
<223> OTHER INFORMATION: sequence of a Flag epitope
```

```
<400> SEQUENCE: 20

Asp Tyr Lys Asp Asp Asp Asp Lys
1               5
```